US012767668B2

(12) United States Patent
Zou et al.

(10) Patent No.: US 12,767,668 B2
(45) Date of Patent: Oct. 20, 2026

(54) IMIDAZOTHIAZOLE COMPOUNDS, PHARMACEUTICAL COMPOSITIONS, AND USES THEREOF

(71) Applicant: GUANGZHOU HENOVCOM BIOSCIENCE CO., LTD., Guangzhou (CN)

(72) Inventors: Qingan Zou, Guangzhou (CN); Jiancun Zhang, Guangzhou (CN); Yanwei Chen, Guangzhou (CN); Lijun Zhang, Guangzhou (CN); Ning Kang, Guangzhou (CN); Chen Guo, Guangzhou (CN)

(73) Assignee: GUANGZHOU HENOVCOM BIOSCIENCE CO., LTD., Guangdong (CN)

( * ) Notice: Subject to any disclaimer, the term of this patent is extended or adjusted under 35 U.S.C. 154(b) by 563 days.

(21) Appl. No.: 18/037,101

(22) PCT Filed: Nov. 15, 2021

(86) PCT No.: PCT/CN2021/130584

§ 371 (c)(1),
(2) Date: May 16, 2023

(87) PCT Pub. No.: WO2022/100727

PCT Pub. Date: May 19, 2022

(65) Prior Publication Data

US 2024/0002401 A1 Jan. 4, 2024

(30) Foreign Application Priority Data

Nov. 16, 2020 (CN) ......................... 202011277302.5

(51) Int. Cl.
*C07D 513/04* (2006.01)
*A61K 45/06* (2006.01)

(52) U.S. Cl.
CPC ............ *C07D 513/04* (2013.01); *A61K 45/06* (2013.01)

(58) Field of Classification Search
CPC .................................................... C07D 513/04
See application file for complete search history.

(56) References Cited

U.S. PATENT DOCUMENTS 10,495,648 B2 * 12/2019 Sarkar .................. C12Q 1/6883
11,679,108 B2 * 6/2023 Zhang .................. A61K 31/496
514/210.16

FOREIGN PATENT DOCUMENTS

CN 110526929 A * 12/2019 ............. A61P 29/00

OTHER PUBLICATIONS

Bartlett "Exploiting Chemical Diversity for Drug Discovery" Edited by Paul A Bartlett and Michael Entzeroth, The Royal Society of Chemistry, 2006, pp. 113-118.*
"Find ETDs Home » Thesis Resources » Find ETDs" Online: "https://ndltd.org/thesis-resources/find-etds/" Accessed Jan. 31, 2023.*
Irwin "ZINC—A Free Database of Commercially Available Compounds for Virtual Screening" J. Chem. Inf. Model. 2005, 45, 177-182.*
Kim "PubChem in 2021: new data content and improved web interfaces" Nucleic Acids Research, 2021, vol. 49, Database issue Published online Nov. 5, 2020.*
STN Registry/ZRegistry (CAS RegistrySM) Sep. 2016 2 pages.*
West, Solid State Chemistry and Its Applications, john Wiley & Sons, 1984, Chapter 10.*
Venkatesh, J. Pharm. Sci. 89, 145-154 (2000) (p. 146, left column).*
J. G. Cannon, Chapter Nineteen in Burger's Medicinal Chemistry and Drug Discovery, Fifth Edition, vol. I: Principles and Practice, Wiley-Interscience 1995, pp. 783-802, 784.*
Ninou, Autotaxin in Pathophysiology and Pulmonary Fibrosis, Front Med (Lausanne). Jun. 13, 2018;5:180.*

* cited by examiner

*Primary Examiner* — Nizal S Chandrakumar
(74) *Attorney, Agent, or Firm* — Houston Beshining Law Office PLLC; Liangang Ye

(57) ABSTRACT

A novel imidazothiazole compound as an Autotaxin inhibitor, a pharmaceutical composition including the compound, and a use thereof in a treatment of a disease with a pathological feature of Autotaxin overexpression in a mammal is provided, wherein the compound has a structure of formula (I), or a pharmaceutically acceptable salt, hydrate, solvate, stereoisomer, tautomer, nitrogen oxide, metabolite, prodrug, or mixture thereof; wherein each of $R^{1a}$, $R^{1c}$, $R^2$, $R^3$, $R^6$, Cy, Y, Z, and t is defined as described in the present disclosure.

(I)

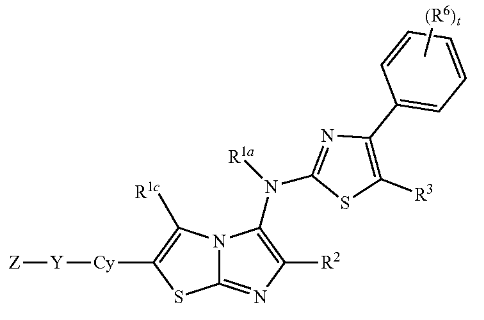

7 Claims, No Drawings

IMIDAZOTHIAZOLE COMPOUNDS, PHARMACEUTICAL COMPOSITIONS, AND USES THEREOF

CROSS-REFERENCE TO RELATED APPLICATIONS

This application claims priority to PCT Application No. PCT/CN2021/130584, having a filing date of Nov. 15, 2021, which is based on Chinese Application No. 202011277302.5, having a filing date of Nov. 16, 2020, the entire contents both of which are hereby incorporated by reference.

FIELD OF TECHNOLOGY

The following relates to the technical field of pharmaceutical chemistry, particularly, it relates to a novel imidazothiazole compound as an Autotaxin (ATX) inhibitor, a pharmaceutical composition comprising the compound and a use thereof in a treatment of a disease with a pathological feature of Autotaxin (ATX) overexpression.

BACKGROUND

Autotaxin (ATX) was first isolated from A2058 melanoma cells in 1992, and is called "autocrine motility factor" and is a secreted glycoprotein. ATX has phosphodiesterase (PDE) activity and is a member of the extracellular pyrophosphatase/phosphodiesterase (ENPP) family. ATX also has lysophospholipase D (lysoPLD) activity and can catalyze the production of lysophosphatidic acid (LPA) using lysophosphatidylcholine (LPC) as a substrate. LPA is not only a precursor for phospholipid synthesis, but also can cause a wide range of biological effects through various signal transduction pathways. Once LPA is produced, it can be mediated by six cell surface-specific receptor proteins (LPA1-6), namely G protein-coupled receptors (GPCR). According to endothelial cell differentiation genes (Edg) and ventricular region genes, LPA1-6 are named as LPA1/Edg-2/VZG-1, LPA2/Edg-4, LPA3/Edg-7, LPA4/p2y9/GPR23, LPA5/GPR92 and LPA6/p2Y5, respectively, and each of the receptors is mediated by Gα proteins (Gs, Gi, Gq, and G12/13), which further triggers a series of cell signaling cascades. The main pathway includes the hydrolysis of phosphatidylinositol diphosphate (PIP2), which triggers the release of intracellular calcium ions and the activation of protein kinase C (PKC); which inhibits the adenylate cyclase (cAMP) signaling pathway; which activates the pathways of Ras-MAPK, MERK, and ERK to regulate the cell proliferation; which activates the phosphoinositide PI3K-AKT pathway to regulate cell survival and apoptosis; finally, which activates the Rho pathway to regulate cytoskeleton remodeling, shape changes and cell migration activities. Under many pathological conditions, especially in tumor cells, ATX has a high expression, resulting in excessive concentration of LPA. In tumor cells, the LPA concentration can increase to 10 μmol/L, which is much higher than the normal level of 100 nmol/L. An excessive amount of LPA increases the production of vascular endothelial growth factor (VEGF) and promotes angiogenesis, which reduces the expression of tumor suppressor p53, and increases tumor cell survival and metastasis. The ATX-LPA signaling pathway involves many physiological and pathological processes, and thus has important links with many serious diseases, mainly including cardiovascular disease, autoimmune disease, cancer, fibrotic disease, inflammatory disease, nervous system disease, pain, etc. LPA has multiple functions in tumor formation, promoting tumor cell growth, angiogenesis, metastasis and the emergence of drug resistance. Therefore, reducing the concentration of LPA is beneficial to the treatment and control of tumors. Correspondingly, inhibiting the activity of AXT and blocking the production pathway of LPA are research hotspots in the treatment of many serious diseases.

With the deepening of research on ATX, many new inhibitors targeting it have emerged, wherein cancer and fibrotic diseases are the most concentrated research. Fibrotic diseases are mainly idiopathic pulmonary fibrosis (IPF) and hepatic fibrosis. IPF is a fatal disease that shows as diffuse alveolitis and alveolar structural disorders and leads to the progressive development of pulmonary interstitial fibrosis; the prognosis is poor, and the average survival time is 2 to 5 years. IPF may be the most closely linked disease with the ATX-LPA pathway, because in lung tissues, the highest expression of ATX is concentrated in bronchial epithelial cells and alveolar macrophages, which can be juxtaposed to fibroblast foci.

At present, GLPG-1690 as an Autotaxin inhibitor has entered a phase II clinical trial, for the treatment of idiopathic pulmonary fibrosis; the concentration of ATX in serum is closely related to hepatic fibrosis and the stiffness of liver, and is one of the best indicators for predicting liver cirrhosis. In addition, ATX has a high expression in many tumor tissues, including melanoma, non-small cell lung cancer, liver cancer, kidney cancer, breast cancer, thyroid cancer, ovarian cancer and Hodgkin's lymphoma. LPA/ATX can promote cell invasion and metastasis during the growth of tumor cells. Therefore, ATX inhibitors block the signal transduction pathway and provide a new way for clinical treatment of cancer and fibrotic diseases.

Compared with the conventional kinase inhibitors, the ATX inhibitors affects multiple signal pathways related to cell proliferation, growth and apoptosis while they are inhibiting the activity of ATX, and they have a better inhibiting effect on some drug-resistant tumors, and are closely related to the fibrogenesis of multiple organs, and they are an important target for the research and development of drugs for novel fibrotic diseases.

The present disclosure provides a novel imidazothiazole compound, which has a good inhibiting activity against ATX and which is even superior to Comparative Embodiment 1 for the enzymatic activity in vitro. In addition, it can be seen from the results of the pharmacokinetics test that the compound of the present disclosure has a higher exposure and bioavailability. In conclusion, the compound of the present disclosure has an excellent efficacy, a perfect pharmaceutical property and/or a good toxicological property and a well clinical prospect.

SUMMARY

An aspect relates to a class of novel imidazothiazole compounds which can have a great inhibiting activity against ATX, as well as a higher exposure and bioavailability in mice, and can be used to prepare a medicament for the treatment of a disease with a pathological feature of ATX over-expression, such as cancer, fibrotic disease (for example, idiopathic pulmonary fibrosis or hepatic fibrosis), metabolic disease, myelodysplastic syndrome, cardiovascular disease, autoimmune disease, inflammatory disease, nervous system disease or pain. It is another aspect to provide a method of preparing the compounds of the present disclosure, a method of treating the above-mentioned diseases in a mammal, especially in humans by applying such compounds, and a pharmaceutical composition including these compounds.

An aspect relates to providing a novel imidazothiazole compound having a structure of formula (I), or a pharmaceutically acceptable salt, hydrate, solvate, stereoisomer, tautomer, nitrogen oxide, metabolite, prodrug, or mixture thereof:

wherein, (I)

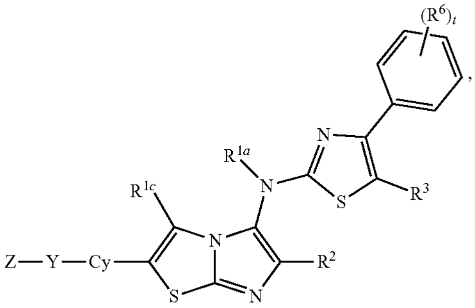

,

Cy is

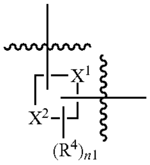

,

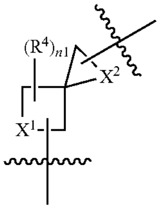

,

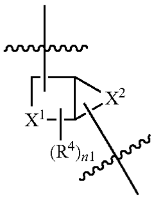

,

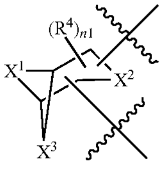

, or

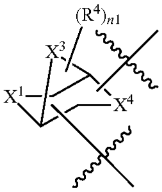

;

Y is —C(═O)—, —N($R^{1b}$)C(═O)—, —S(═O)$_{1-2}$—, —$(CH_2)_{t1}$—, —C(═O)$(CH_2)_{t1}$—, —N($R^{1b}$)C(═O)—$(CH_2)_{t1}$—, —$(CH_2)_{t2}$—N($R^{1b}$)C(═O)—$(CH_2)_{t1}$—, —C(═O)—$CH_2$—N($R^{1b}$)—, or —NHC(═O)NH—;

Z is H, —CN, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, $C_{3-8}$ cycloalkyl, $C_{2-7}$ heterocyclyl, $C_{2-7}$ heterocyclyl-$C_{1-6}$ alkyl, $C_{3-8}$ cycloalkyl-$C_{1-6}$ alkyl, $C_{6-10}$ aryl, or $C_{1-9}$ heteroaryl, wherein Z is optionally substituted with one or more $R^5$;

each of $X^1$, $X^2$, and $X^3$ is independently —O—, —S—, —NH—, —$(CH_2)_{m1}$—NH—$(CH_2)_{m2}$—, —$(CH_2)_{m1}$—O—$(CH_2)_{m2}$—, —$(CH_2)_{m1}$—S—$(CH_2)_{m2}$—, —C(═O)—, —C(═O)$NR^8$—, —S(═O)$_{1-2}$—, or —$(CH_2)_{m3}$—;

$R^{1a}$ is H, $C_{2-6}$ alkyl, $C_{1-6}$ haloalkyl, $C_{1-6}$ hydroxyalkyl, $C_{3-6}$ cycloalkyl, or $C_{3-6}$ cycloalkyl-$C_{1-6}$ alkyl, wherein each of the $C_{2-6}$ alkyl, $C_{1-6}$ haloalkyl, $C_{1-6}$ hydroxyalkyl, $C_{3-6}$ cycloalkyl, or $C_{3-6}$ cycloalkyl-$C_{1-6}$ alkyl is optionally substituted with 1, 2, 3, 4, or 5 substituents independently selected from H, D, oxo(C═O), —CN, —$NO_2$, —OH, —$NH_2$, —$N_3$, F, Cl, Br, or I;

$R^{1b}$ is H, $C_{1-4}$ alkyl, $C_{3-6}$ cycloalkyl, or $C_{3-6}$ cycloalkyl-$C_{1-4}$ alkyl, wherein $R^{1b}$ is optionally substituted with 1, 2, 3, or 4 $R^7$;

$R^{1c}$ is H, F, Cl, Br, I, —CN, —C(═O)$NHR^8$, —$CF_2H$, —$CF_3$, —C(═O)$OR^8$, —$NO_2$, —S(═O)$_{1-2}OR^8$, $C_{1-3}$ alkyl, $C_{2-3}$ alkenyl, or $C_{2-3}$ alkynyl;

$R^2$ is H, —CN, —$NO_2$, —OH, —$NH_2$, —$N_3$, F, Cl, Br, I, $C_{1-4}$ alkyl, $C_{1-4}$ haloalkyl, or $C_{1-4}$ hydroxyalkyl;

$R^3$ is H, —CN, —$NO_2$, —OH, —$NH_2$, —$N_3$, F, Cl, Br, I, $C_{1-6}$ alkyl, $C_{2-6}$ alkenyl, $C_{2-6}$ alkynyl, $C_{1-6}$ haloalkyl, $C_{1-6}$ cyanoalkyl, or $C_{1-6}$ hydroxyalkyl;

each of $R^4$, $R^5$, $R^6$, $R^7$, and $R^8$ is, independently in each instance, H, D, oxo (C═O), —CN, —$NO_2$, —OH, —$NH_2$, —$N_3$, F, Cl, Br, I, $C_{1-6}$ alkyl, $C_{1-6}$ haloalkyl, $C_{1-6}$ cyanoalkyl, $C_{1-6}$ hydroxyalkyl, $C_{1-6}$ alkoxy, $C_{1-6}$ haloalkoxy, or $C_{1-6}$ haloalkoxy-$C_{1-6}$ alkyl;

each of m1 is, independently in each instance, 1, 2, or 3;

each of m2 is, independently in each instance, 0, 1, 2, or 3;

each of m3 is, independently in each instance, 1, 2, or 3;

n1 is 0, 1, 2, 3, or 4;

t is 0, 1, 2, 3, or 4; and each of t1 and t2 is independently 1, 2, 3, or 4.

In another aspect, the present disclosure provides a pharmaceutical composition, comprising the compound of the present disclosure or a pharmaceutically acceptable salt, hydrate, solvate, stereoisomer, tautomer, nitrogen oxide, metabolite, prodrug thereof, and a pharmaceutically acceptable excipient, diluent, or carrier.

In some embodiments, the pharmaceutical composition of the present disclosure further comprises an additional therapeutic agent.

In another aspect, the present disclosure provides a use of the compound or the pharmaceutical composition of the present disclosure in the preparation of a medicament for preventing or treating a disease with a pathological feature of Autotaxin (ATX) overexpression in a mammal.

In some embodiments, the disease with a pathological feature of Autotaxin overexpression comprises: cancer, fibrotic disease, metabolic disease, myelodysplastic syndrome, cardiovascular disease, autoimmune disease, inflammatory disease, nervous system disease, or pain.

In some embodiments, the disease with a pathological feature of Autotaxin overexpression is idiopathic pulmonary fibrosis or hepatic fibrosis.

DETAILED DESCRIPTION

Definition and General Terms

All the scientific and technological terms used in the present disclosure have the same meaning as commonly understood by those skilled in the conventional art to which the present disclosure belongs, unless otherwise stated. All patents and publications related to the present disclosure are incorporated into the present disclosure by reference in their entirety.

Unless otherwise stated, the following definitions used herein shall be applied. For the purpose of the present disclosure, Periodic Table with all the elements in CAS version is consistent with "Handbook of Chemistry and Physics", 75th edition, 1994. In addition, the general principles of organic chemistry can refer to the descriptions in "*Organic Chemistry*", Thomas Sorrell, University Science Books. Susalito: 1999, and "*March's Advanced Organic Chemistry*" by Michael B. Smith and Jerry March, John Wiley & Sons, New York: 2007, the entire contents of which are incorporated herein by reference.

Unless otherwise stated or there is an obvious conflict in context, the articles "a", "an" and "the" used herein are intended to include "at least one" or "one or more". Therefore, these articles used herein refer to articles of one or more than one (i.e., at least one) objects. For example, "a component" means one or more components, that is, more than one component may be considered to be applied or used in the embodiment of the technical solution.

"Stereoisomers" refer to compounds having the same chemical structure, but different arrangement of the atoms or groups in space. The stereoisomers include enantiomers, diastereomers, conformational isomers (rotational isomers), geometrical isomers (cis/trans isomers), atropisomers, etc.

In general, the term "substituted" means that one or more hydrogen atoms in a given structure are replaced by a specified substituent. Unless otherwise stated, one substituted group can have a substituent at each substitutable position of the group. When more than one position in the given structural formula can be substituted by one or more substituents selected from a specific group, then the substituents can be substituted at each position with the same or different substitutions.

The term "unsubstituted" indicates that the specified group does not have any substituent.

The term "optionally substituted . . . with" and the term "unsubstituted or substituted . . . with" are interchangeable, that is, the structure is unsubstituted or substituted with one or more substituents of the present disclosure. The substituents of the present disclosure include, but are not limited to, H, D, oxo (C═O), —CN, —$NO_2$, —OH, —$NH_2$, —$N_3$, F, Cl, Br, I, alkyl, haloalkyl, cyanoalkyl, hydroxy alkyl, aminoalkyl, alkoxy, alkylamino, haloalkoxy, or haloalkoxyalkyl, etc.

In addition, it should be noted that, unless otherwise expressly stated, the description ways used in the present disclosure such as "each of . . . is independently selected from . . . " and "are each independently selected from "and" . . . are independently" are interchangeable and should be understood in broad sense. It may mean that specific options expressed on the same symbol in different groups do not affect each other, and it also may mean that specific options expressed on the same symbol in the same group do not affect each other.

In each part of the description of the present disclosure, the substituents of the compounds disclosed in the present disclosure are disclosed according to the type or scope of the group. In particular, the present disclosure includes each independent subcombination of each member of the type and scope of these groups. For example, the term "$C_{1-6}$ alkyl" specifically refers to independently disclosed methyl, ethyl, $C_3$ alkyl, $C_4$ alkyl, $C_5$ alkyl, and $C_6$ alkyl.

The term "alkyl" or "alkyl group" used herein means a saturated linear or branched monovalent hydrocarbon group containing 1 to 20 carbon atoms, wherein the alkyl group may be optionally substituted with one or more substituents described herein. Unless otherwise specified, the alkyl group contains 1 to 20 carbon atoms. In one embodiment, the alkyl group contains 1 to 12 carbon atoms; in another embodiment, the alkyl group contains 1 to 6 carbon atoms; in a further embodiment, the alkyl group contains 1 to 4 carbon atoms; in yet another embodiment, the alkyl group contains 1 to 3 carbon atoms. The alkyl group may be optionally substituted with one or more substituents described herein.

Embodiments of the alkyl group include, but are not limited to, methyl (Me, —$CH_3$), ethyl (Et, —$CH_2CH_3$), n-propyl (n-Pr, —$CH_2CH_2CH_3$), isopropyl (i-Pr, —$CH(CH_3)_2$), n-butyl (n-Bu, —$CH_2CH_2CH_2CH_3$), isobutyl (i-Bu, —$CH_2CH(CH_3)_2$), sec-butyl (s-Bu, —$CH(CH_3)CH_2CH_3$), tert-butyl (t-Bu, —$C(CH_3)_3$), n-pentyl (—$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), n-hexyl (—$CH_2CH_2CH_2CH_2CH_2CH_3$), 2-hexyl (— $CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), n-heptyl, n-octyl, etc.

The term "alkyl-D" or "ethyl-D" refers to alkyl group or ethyl group substituted with 1, 2, 3, 4, 5, or 6 D atoms, wherein the alkyl group is defined as described in the present disclosure. The embodiments of alkyl-D or ethyl-D include, but are not limited to —$CD_3$, —$CH_2D$, —$CHD_2$, —$CD_2CD_3$, —$CH_2CD_3$, or —$CD_2CH_3$, etc.

The term "alkoxy" means that the alkyl group is connected to the rest of the molecule through an oxygen atom, wherein the alkyl group has the definition as described herein. Unless otherwise specified, the alkoxy group contains 1 to 12 carbon atoms. In one embodiment, the alkoxy group contains 1 to 6 carbon atoms; in another embodiment, the alkoxy group contains 1 to 4 carbon atoms; in a further embodiment, the alkoxy group contains 1 to 3 carbon atoms. The alkoxy group may be optionally substituted with one or more substituents described herein.

Embodiments of alkoxy group include, but are not limited to, methoxy (MeO, —$OCH_3$), ethoxy (EtO, —$OCH_2CH_3$), 1-propoxy (n-PrO, n-propoxy, —$OCH_2CH_2CH_3$), 2-propoxy (i-PrO, i-propoxy, —$OCH(CH_3)_2$), 1-butoxy (n-BuO, n-butoxy, —$OCH_2CH_2CH_2CH_3$), 2-methyl-1-propoxy (i-BuO, i-butoxy, —$OCH_2CH(CH_3)_2$), 2-butoxy (s-BuO, s-butoxy, —$OCH(CH_3)CH_2CH_3$), 2-methyl-2-propoxy (t-BuO, t-butoxy, —$OC(CH_3)_3$), 1-pentoxy (n-pentoxy, —$OCH_2CH_2CH_2CH_2CH_3$), 2-pentyloxy (—$OCH(CH_3)CH_2CH_2CH_3$), 3-pentyloxy (—$OCH(CH_2CH_3)_2$), 2-methyl-2-butoxy (—$OC(CH_3)_2CH_2CH_3$), 3-methyl-2-butoxy (—$OCH(CH_3)CH(CH_3)_2$), 3-methyl-1-butoxy (—$OCH_2CH_2CH(CH_3)_2$), 2-methyl-1-butoxy (—$OCH_2CH(CH_3)CH_2CH_3$), etc.

The term "haloalkyl", "haloalkenyl" or "haloalkoxy" means an alkyl, alkenyl or alkoxy group substituted with one or more halogen atoms. Embodiments of the haloalkyl, haloalkenyl, or haloalkoxy group include, but are not limited to, trifluoromethyl, trifluoroethyl, 2,2,3,3-tetrafluoropropyl, trifluoromethoxy, etc.

The term "hydroxyalkyl" or "hydroxy-substituted alkyl" used herein means that an alkyl group is substituted with one or more hydroxy groups, wherein the alkyl group is defined as described herein. Embodiments of the hydroxyalkyl group include, but are not limited to, hydroxy ethyl, 2-hydroxypropyl, hydroxymethyl, etc.

The term "cycloalkyl" used herein, unless otherwise specified, refers to a monovalent saturated or partially unsaturated (but not aromatic) monocyclic or polycyclic hydrocarbon. In some embodiments, the cycloalkyl group may be a bridged or unbridged, spiro cyclic or non-spiro cyclic, and/or fused or non-fused bicyclic. In some embodiments, the cycloalkyl group includes 3 to 10 carbon atoms, i.e., $C_3$ to $C_{10}$ cycloalkyl. In some embodiments, the cycloalkyl group has 3 to 15 ($C_{3-15}$), 3 to 10 ($C_{3-10}$), or 3 to 7 ($C_{3-7}$) carbon atoms. In some embodiments, the cycloalkyl group is monocyclic or bicyclic. In some embodiments, the cycloalkyl group is monocyclic. In some embodiments, the cycloalkyl group is bicyclic. In some embodiments, the cycloalkyl group is tricyclic. In some embodiments, the cycloalkyl group is fully saturated. In some embodiments, the cycloalkyl group is partially saturated. In some embodiments, the cycloalkyl group is cyclopropyl, cyclobutyl, cyclopentyl, cyclohexyl, cycloheptyl, bicyclo[2.1.1]hexyl, bicyclo[2.2.1]heptyl, decahydronaphthyl, or adamantyl. When a cycloalkyl group is substituted, it can be on any ring, that is, on any aromatic or non-aromatic ring contained by the cycloalkyl group, and it is independently substituted with one or more substituents described herein.

The terms "heterocyclyl" and "heterocycle" are used interchangeably herein, and unless otherwise specified, they refer to a monovalent monocyclic non-aromatic ring system and/or polycyclic ring system containing at least one non-aromatic ring, wherein the non-aromatic monocyclic atoms comprise one or more heteroatoms (in some embodiments, there being 1, 2, 3, or 4 heteroatoms) independently selected from O, $S(O)_{0-2}$ and N, and the remaining ring atoms are all carbon atoms; and wherein the ring atoms in the polycyclic ring system comprise one or more heteroatoms (in some embodiments, there being 1, 2, 3, or 4 heteroatoms) independently selected from O, $S(O)_{0-2}$ and N, and the remaining ring atoms are all carbon atoms. In some embodiments, the heterocyclyl contains 1 or 2 heteroatoms, which are nitrogen atoms. In some embodiments, the heterocyclyl is polycyclic and contains one heteroatom in a non-aromatic ring, or contains one heteroatom in an aromatic ring, or contains two heteroatoms in an aromatic ring, or contains two heteroatoms, one an aromatic ring and the other in a non-aromatic ring. In some embodiments, the heterocyclyl group has 3 to 20, 3 to 15, 3 to 10, 3 to 8, 4 to 7, or 5 to 6 ring atoms. In some embodiments, the heterocyclyl group is a monocyclic, bicyclic, tricyclic, or tetracyclic ring system. In some embodiments, the heterocyclyl group may be a bridged or unbridged, spiro cyclic or non-spiro cyclic, and/or fused or non-fused bicyclic. One or more nitrogen atoms and sulfur atoms can be optionally oxidized, and one or more nitrogen atoms can be optionally quaternized, and one or more carbon atoms can be optionally substituted with

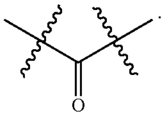 [SMILES: *C(*)=O]

Some rings may be partially or fully saturated, or aromatic, provided that the heterocycle is not fully aromatic. The monocyclic heterocycle and polycyclic heterocycle may be connected to the main structure at any heteroatoms or carbon atoms that result in a steady compound. The polycyclic heterocyclyl can be connected to the main structure through any ring, including any aromatic or non-aromatic ring, regardless of whether the ring contains a heteroatom or not. In some embodiments, the heterocyclyl is a "heterocycloalkyl group", which is 1) a saturated or partially unsaturated (but not aromatic) monovalent monocyclic group containing at least one heterocycloatom as described herein, or 2) saturated or partially unsaturated (but not aromatic) monovalent bicyclyl or tricyclic group, wherein at least one ring contains at least one heteroatom as described herein. When the heterocyclyl and heterocycloalkyl group are substituted, they can be substituted on any ring, that is, on any aromatic or non-aromatic ring contained by the heterocyclyl and heterocycloalkyl group. In some embodiments, such heterocyclyl group includes, but is not limited to, epoxyethanyl, azetidinyl, oxetanyl, thietanyl, pyrrolidinyl, 2-pyrrolinyl, 3-pyrrolinyl, pyrazolinyl, pyrazolidinyl, imidazolinyl, imidazolidinyl, tetrahydrofuranyl, dihydrofuranyl, tetrahydrothienyl, dihydrothienyl, 1,3-dioxolanyl, dithiolanyl, tetrahydropyranyl, dihydropyranyl, 2H-pyranyl, 4H-pyranyl, tetrahydrothiopyranyl, piperidinyl, morpholinyl, thiomorpholinyl, piperazinyl, dioxanyl, dithianyl, thioxanyl, homopiperazinyl, homopiperidinyl, oxepanyl, thiepanyl, oxazepinyl, diazepinyl, thiazepinyl, benzodioxanyl, benzodioxolyl, benzofuranone, benzopyranone, benzopyranyl, dihydrobenzofuranyl, benzotetrahydrothienyl, benzothiopyranyl, benzoxazinyl, β-carbolinyl, benzopyranyl, chromonyl, cinnolyl, coumaryl, decahydroquinolinyl, decahydroisoquinolinyl, dihydrobenzisothiazinyl, dihydrobenzisoxazinyl, dihydrofuranyl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithiopyranyl, furanonyl, imidazolidinyl, 2,4-dioxo-imidazolidinyl, imidazolinyl, indolinyl, 2-oxo-indolinyl, isobenzotetrahydrofuranyl, isobenzotetrahydrothienyl, isobenzodihydropyranyl, isocoumarinyl, isodihydroindolyl (isoindolinyl), 1-oxo-isodihydroindolyl, 1,3-dioxo-isodihydroindolyl, isothiazolidinyl, isoxazolidinyl, 3-oxo-isoxazolidinyl, morpholinyl, 3,5-dioxo-morpholinyl, octahydroindolyl, octahydroisoindolyl, 1-oxo-octahydroisoindolyl, 1,3-dioxo-hexahydroisoindolyl, oxazolidinonyl, oxazolidinyl, oxiranyl, piperazinyl, 2,6-dioxo-piperazinyl, piperidinyl, 2,6-dioxo-piperidinyl, 4-piperidinone, 2-oxopyrrolidinyl, 2,5-dioxopyrrolidinyl, quinuclidinyl, tetrahydroisoquinolinyl, 3,5-dioxo-thiomorpholinyl, thiazolidinyl, 2,4-dioxo-thiazolidinyl, tetrahydroquinolinyl, phenothiazinyl, phenoxazinyl, xanthene and 1,3,5-trithiocyclohexyl. Embodiments of the $-CH_2-$ group in the heterocyclyl substituted with $-C(=O)-$ include, but are not limited to, 2-oxopyrrolidinyl, oxo-1,3-thiazolidinyl, 2-piperidone, 3,5-dioxopiperidinyl and pyrimidinedione. Embodiments of sulfur atom oxidized in the heterocyclyl include, but are not limited to, sulfolanyl and a 1,1-dioxothiomorpholinyl. The heterocyclyl may be optionally substituted with one or more substituents described herein.

In one embodiment, the heterocycyl is a heterocyclyl composed of 3 to 8 atoms, and refers to a saturated or partially unsaturated monocyclic ring containing 3 to 8 ring atoms, wherein at least one ring atom is selected from nitrogen, sulfur and oxygen atoms. Unless otherwise specified, the heterocyclyl consisting of 3 to 8 atoms may be a carbon group or a nitrogen group, and the $-CH_2-$ group may be optionally substituted with $-C(=O)-$. The sulfur atom of the ring can optionally be oxidized to S-oxide. The nitrogen atom of the ring can optionally be oxidized to an N-oxide. Embodiments of heterocyclyl consisting of 3 to 8 atoms include, but are not limited to, azetidinyl, oxetanyl, thietanyl, pyrrolidinyl, 2-pyrrolinyl, 3-pyrrolinyl, pyrazolinyl, pyrazolidinyl, imidazolinyl, imidazolidinyl, tetrahydrofuranyl, dihydrofuranyl, tetrahydrothienyl, dihydrothienyl, 1,3-dioxolanyl, dithiolanyl, tetrahydropyranyl, dihydropyranyl, 2H-pyranyl, 4H-pyranyl, tetrahydrothiopyranyl, piperidinyl, morpholinyl, thiomorpholinyl, piperazinyl, dioxanyl, dithianyl, thioxanyl, homopiperazinyl, homopiperidinyl, oxepanyl, thiepanyl, oxazepinyl, diazepinyl, thiazepinyl. Embodiments of $—CH_2—$ group in the heterocyclyl substituted with —C(=O)— include, but are not limited to, 2-oxopyrrolidinyl, oxo-1,3-thiazolidinyl, 2-piperidinonyl, 3,5-dioxopiperidinyl and pyrimidinedionyl. Embodiments of sulfur atom in the heterocyclyl oxidized include, but are not limited to, sulfolanyl and 1,1-dioxothiomorpholinyl. The heterocyclyl consisting of 3 to 8 atoms can be optionally substituted with one or more substituents described herein.

In one embodiment, the heterocyclyl is a heterocyclyl consisting of 3 to 6 atoms, and refers to a saturated or partially unsaturated monocyclic ring containing 3 to 6 ring atoms, wherein at least one ring atom is selected from nitrogen, sulfur and oxygen atoms. Unless otherwise specified, the heterocyclyl consisting of 3 to 6 atoms may be a carbon group or a nitrogen group, and the $—CH_2—$ group may be optionally substituted with —C(=O)—. The sulfur atom of the ring can optionally be oxidized to S-oxide. The nitrogen atom of the ring can optionally be oxidized to an N-oxide. The heterocyclyl consisting of 3 to 6 atoms can be optionally substituted with one or more substituents described herein.

In another embodiment, the heterocyclyl is a heterocyclyl consisting of 5 to 6 atoms, and refers to a saturated or partially unsaturated monocyclic ring containing 5 to 6 ring atoms, wherein at least one ring atom is selected from nitrogen, sulfur and oxygen atoms. Unless otherwise specified, the heterocyclyl consisting of 5 to 6 atoms may be a carbon group or a nitrogen group, and the $—CH_2—$ group may be optionally substituted with —C(=O)—. The sulfur atom of the ring can optionally be oxidized to S-oxide. The nitrogen atom of the ring can optionally be oxidized to an N-oxide. Embodiments of heterocyclyl consisting of 5 to 6 atoms include, but are not limited to, pyrrolidinyl, 2-pyrrolinyl, 3-pyrrolinyl, pyrazolinyl, pyrazolidinyl, imidazolinyl, imidazolidinyl, tetrahydrofuranyl, dihydrofuranyl, tetrahydrothienyl, dihydrothienyl, 1,3-dioxocyclopentyl, dithiocyclopentyl, 2-oxopyrrolidinyl, oxo-1,3-thiazolidinyl, sulfolanyl, tetrahydropyranyl, dihydropyranyl, 2H-pyranyl, 4H-pyranyl, tetrahydrothiopyranyl, piperidinyl, morpholinyl, thiomorpholinyl, piperazinyl, dioxanyl, dithianyl, thioxanyl, 2-piperidinonyl, 3,5-dioxopiperidinyl and pyrimidinedionyl, 1,1-dioxylthiomorpholinyl. The heterocyclyl consisting of 5 to 6 atoms may be optionally substituted with one or more substituents described herein.

The term "cycloalkylalkyl" means that the alkyl group may be substituted with one or more cycloalkyl groups, wherein the cycloalkyl and alkyl are defined as described herein. Embodiments of cycloalkylalkyl include, but are not limited to, cyclopropylmethyl, cyclopropylethyl, cyclopropylpropyl, cyclobutylmethyl, cyclobutylethyl, cyclopentylmethyl, cyclopentylethyl, cyclopentylpropyl, cyclohexylethyl, etc.

The term "heterocyclylalkyl" includes heterocyclyl-substituted alkyl; the term "heterocyclylalkoxy" includes heterocyclyl-substituted alkoxy, wherein the oxygen atom is connected to the rest of the molecule; the term "heterocyclylalkylamino" includes heterocyclyl-substituted alkylamino, wherein the nitrogen atom is connected to the rest of the molecule, wherein heterocyclyl, alkyl group, alkoxy group and alkylamino group are all defined as described herein. Embodiments of heterocyclylalkylamino include, but are not limited to, azetidine-1-ylmethyl, azetidine-1-ylethyl, azetidine-1-ylpropyl, pyrrol-1-ylmethyl, pyrrol-1-ylethyl, pyrrol-1-ylpropyl, morpholin-4-ylethyl, morpholin-4-ylethoxy, piperazin-4-ylethoxy, piperidin-4-ylethylamino, etc.

As described in the present disclosure, there are two connection points connected to the rest of the molecule in a ring system, as shown in formula (a1) or (a2), meaning either E end or E' end is connected to the rest of the molecule, i.e., the connection of the two ends can be interchangeable.

(a1)

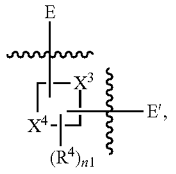

(a2)

$E—N(R^g)C(=O)O—E'$

The term "consisting of n atoms" typically describes the number of ring atoms in the molecule, and the number of ring atoms in the molecule is n, wherein n is an integer. For example, piperidinyl is a heterocycloalkyl group consisting of 6 atoms, and 1,2,3,4-tetrahydronaphthalene is a cycloalkyl group consisting of 10 atoms.

The term "heteroatom" refers to O, S, N, P and Si, comprising N, S, P in any oxidation state; primary, secondary, tertiary and quaternary ammonium salt forms; or the form wherein the hydrogen on the nitrogen atom in the heterocycle is substituted, for example, N (like N in 3,4-dihydro-2H-pyrrolyl), NH (like NH in pyrrolidinyl) or NR (like NR in N-substituted pyrrolidinyl).

The term "cyano-substituted alkyl" or "cyanoalkyl" includes $C_{1-10}$ straight or branched chain alkyl groups substituted with one or more cyano groups. In some embodiments, the cyanoalkyl group is a $C_{1-6}$ "lower cyanoalkyl" substituted with one or more cyano groups, and in other embodiments, the cyanoalkyl group is a $C_{1-4}$ "lower cyanoalkyl group" substituted with one or more cyano groups. Such embodiments include, but are not limited to, $CNCH_2—$, $CNCH_2CH_2—$, $CNCH_2CH_2CH_2—$, $CNCH_2CHCNCH_2—$, etc.

As described in the present disclosure, the ring system (as shown in the figure below), formed by attaching a substituent through drawing a bond to the central ring, represents that the substituent can be substituted at any substitutable position on any rings. For example, formula b represents that any position on ring A or ring B that may be substituted, such as formula c, d, e, f, g, h, i, j, k, l, m, n, o, p, q, etc.

b

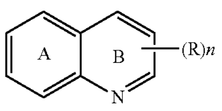

c

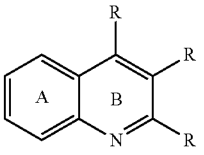

-continued d

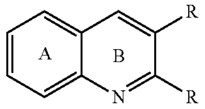

e

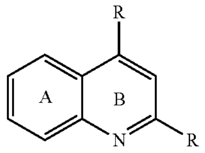

f

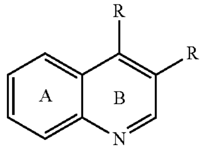

g

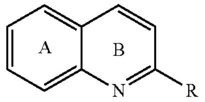

h

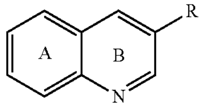

i

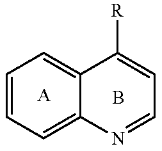

j

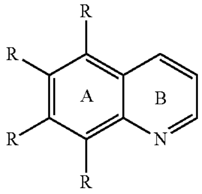

k

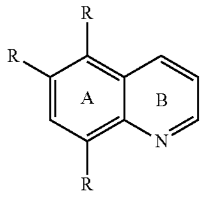

l

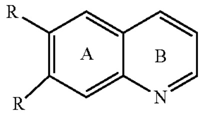

m

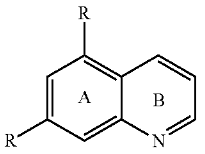

-continued n

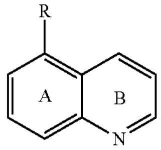

o

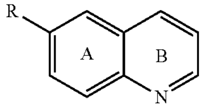

p

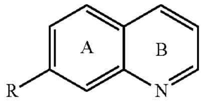

q

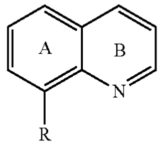

The term "pharmaceutically acceptable salt" used in the present disclosure refers to organic salts and inorganic salts of the compound of the present disclosure. The pharmaceutically acceptable salts are well known for one skilled in the field, as described in the literature: S. M. Berge et al., describe pharmaceutically acceptable salts n detail in *J. Pharmaceutical Sciences,* 1977, 66: 1-19. The pharmaceutically acceptable non-toxicsalts formed by acid include, but are not limited to, inorganic acid salts formed by reaction with amino groups such as hydrochloride, hydrobromide, phosphate, sulfate, and perchlorate, and organic acid salts, such as acetate, oxalate, maleate, tartrate, citrate, succinate, malonate, or other salts formed by methods described in books and literatures such as ion exchange. Other pharmaceutically acceptable salts include adipate, alginate, ascorbate, aspartate, benzene sulfonate, benzoate, bisulfate, borate, butyrate, camphanate, camphorsulfonate, cyclopentylpropionate, digluconate, laurylsulfonate, ethanesulfonate, formate, fumarate, gluceptate, glycerophosphate, gluconate, hemisulfate, enanthate, hexanoate, hydriodate, 2-hydroxy-ethanesulfonate, lactobionate, lactate, laurate, laurylsulfate, malate, malonate, mesylate, 2-naphthalenesulfonate, nicotinate, nitrate, oleate, palmitate, embonate, pectate, persulphate, 3-phenylpropionate, picrate, pivalate, propionate, stearate, thiocyanate, tosilate, undecanoate, valerate, etc. The salts obtained by reaction with suitable alkali include alkaline metal, alkaline earth metal, ammonium and $N^+(C_1\sim C_4\ alkyl)_4$ salts. The present disclosure also designs the quaternary ammonium salt formed by any compound containing the N group. Water-soluble or oil-soluble or dispersed products can be obtained by quaternization. The alkaline metal or alkaline earth metal salts include sodium, lithium, potassium, calcium, magnesium, etc. The pharmaceutically acceptable salts further include appropriate, non-toxic ammonium, quaternary ammonium salts and amine cation formed by anti-equilibrium ion, such as halides, hydroxides, carboxylates, sulfates, phosphates, nitrates, $C_{1-8}$ sulfonates and aromatic sulfonates.

The "solvate" of the present disclosure refers to the association complex formed by one or more solvent molecules and the compounds of the present disclosure. The solvents that form solvates include, but are not limited to, water, isopropanol, ethanol, methanol, dimethyl sulfoxide, ethyl acetate, acetic acid, and aminoethanol. The term “hydrate” refers to an association complex formed by the solvent molecule, which is water.

When the solvent is water, the term “hydrate” can be used. In some embodiments, a compound of the present disclosure can be connected to one water molecule, such as monohydrate; in further embodiments, a compound of the present disclosure can be connected to more than one water molecules, such as dihydrate, and in yet another embodiments, a compound of the present disclosure can be connected to less than one water molecule, such as hemihydrate. It should be noted that the hydrates of the present disclosure retain the biologically effectiveness of the compound in its non-hydrated form.

SUMMARY

An aspect relates to providing a imidazothiazole compound, which can effectively inhibit the activity of ATX, and for the enzymatic activity in vitro, a great number of the compounds are superior to Comparative Embodiment 1 and have higher exposure and bioavailability in mice, and therefore the compounds can be used to prepare a medicament for the treatment of a disease with a pathological feature of ATX over-expression, such as cancer, fibrotic disease (for example, idiopathic pulmonary fibrosis or hepatic fibrosis), metabolic disease, myelodysplastic syndrome, cardiovascular disease, autoimmune disease, inflammatory disease, nervous system disease, or pain.

An aspect relates to providing an imidazothiazole compound having a structure of formula (I), or a pharmaceutically acceptable salt, hydrate, solvate, stereoisomer, tautomer, nitrogen oxide, metabolite, prodrug, or mixture thereof:

(I)

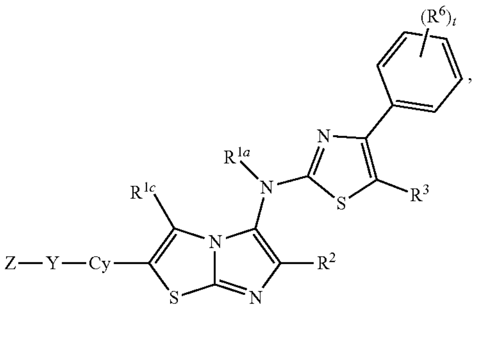

, wherein,

Cy is

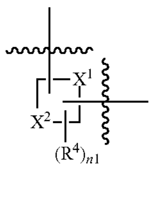

,

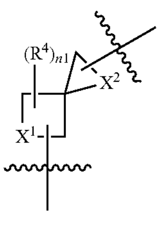

,

-continued

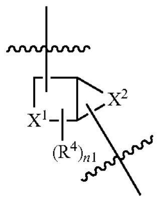

,

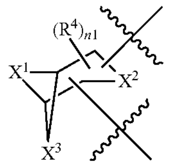

, or

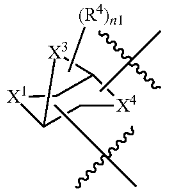

;

Y is $-C(=O)-$, $-N(R^{1b})C(=O)-$, $-S(=O)_{1-2}-$, $-(CH_2)_{t1}-$, $-C(=O)(CH_2)_{t1}-$, $-N(R^{1b})C(=O)-(CH_2)_{t1}-$, $-(CH_2)_{t2}-N(R^{1b})C(=O)-(CH_2)_{t1}-$, $-C(=O)-CH_2-N(R^{1b})-$, or $-NHC(=O)NH-$;

Z is H, —CN, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, $C_{3-8}$ cycloalkyl, $C_{2-7}$ heterocyclyl, $C_{2-7}$ heterocyclyl-$C_{1-6}$ alkyl, $C_{3-8}$ cycloalkyl-$C_{1-6}$ alkyl, $C_{6-10}$ aryl, or $C_{1-9}$ heteroaryl, wherein Z is optionally substituted with one or more $R^5$;

each of $X^1$, $X^2$, and $X^3$ is independently —O—, —S—, —NH—, $-(CH_2)_{m1}-NH-(CH_2)_{m2}-$, $-(CH_2)_{m1}-O-(CH_2)_{m2}-$, $-(CH_2)_{m1}-S-(CH_2)_{m2}-$, $-C(=O)-$, $-C(=O)NR^8-$, $-S(=O)_{1-2}-$, or $-(CH_2)_{m3}-$;

$R^{1a}$ is H, $C_{2-6}$ alkyl, $C_{1-6}$ haloalkyl, $C_{1-6}$ hydroxyalkyl, $C_{3-6}$ cycloalkyl, or $C_{3-6}$ cycloalkyl-$C_{1-6}$ alkyl, wherein each of the $C_{2-6}$ alkyl, $C_{1-6}$ haloalkyl, $C_{1-6}$ hydroxyalkyl, $C_{3-6}$ cycloalkyl, or $C_{3-6}$ cycloalkyl-$C_{1-6}$ alkyl is optionally substituted with 1, 2, 3, 4, or 5 substituents independently selected from H, D, oxo(C=O), —CN, $-NO_2$, —OH, $-NH_2$, $-N_3$, F, Cl, Br, or I;

$R^{1b}$ is H, $C_{1-4}$ alkyl, $C_{3-6}$ cycloalkyl, or $C_{3-6}$ cycloalkyl-$C_{1-4}$ alkyl, wherein $R^{1b}$ is optionally substituted with 1, 2, 3, or 4 $R^7$;

$R^{1c}$ is H, F, Cl, Br, I, —CN, $-C(=O)NHR^8$, $-CF_2H$, $-CF_3$, $-C(=O)OR^8$, $-NO_2$, $-S(=O)_{1-2}OR^8$, $C_{1-3}$ alkyl, $C_{2-3}$ alkenyl, or $C_{2-3}$ alkynyl;

$R^2$ is H, —CN, $-NO_2$, —OH, $-NH_2$, $-N_3$, F, Cl, Br, I, $C_{1-4}$ alkyl, $C_{1-4}$ haloalkyl, or $C_{1-4}$ hydroxyalkyl;

$R^3$ is H, —CN, $-NO_2$, —OH, $-NH_2$, $-N_3$, F, Cl, Br, I, $C_{1-6}$ alkyl, $C_{2-6}$ alkenyl, $C_{2-6}$ alkynyl, $C_{1-6}$ haloalkyl, $C_{1-6}$ cyanoalkyl, or $C_{1-6}$ hydroxyalkyl;

each of $R^4$, $R^5$, $R^6$, $R^7$, and $R^8$ is, independently in each instance, H, D, oxo (C=O), —CN, $-NO_2$, —OH, $-NH_2$, $-N_3$, F, Cl, Br, I, $C_{1-6}$ alkyl, $C_{1-6}$ haloalkyl, $C_{1-6}$ cyanoalkyl, $C_{1-6}$ hydroxyalkyl, $C_{1-6}$ alkoxy, $C_{1-6}$ haloalkoxy, or $C_{1-6}$ haloalkoxy-$C_{1-6}$ alkyl;

each of m1 is, independently in each instance, 1, 2, or 3;

each of m2 is, independently in each instance, 0, 1, 2, or 3;

each of m3 is, independently in each instance, 1, 2, or 3;

n1 is 0, 1, 2, 3, or 4;

t is 0, 1, 2, 3, or 4; and each of t1 and t2 is independently 1, 2, 3, or 4.

In some embodiments, the compound of the present disclosure has a structure of formula (II):

(II)

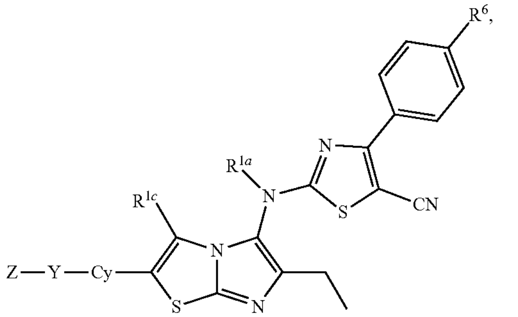

or a pharmaceutically acceptable salt, hydrate, solvate, stereoisomer, tautomer, nitrogen oxide, metabolite, prodrug, or mixture thereof.

In some embodiments, $R^{1a}$ is H, $C_{2-4}$ alkyl, $C_{1-4}$haloalkyl, $C_{1-4}$ hydroxyalkyl, $C_{3-6}$ cycloalkyl, or $C_{3-6}$ cycloalkyl-$C_{1-4}$ alkyl, wherein each of the $C_{2-4}$ alkyl, $C_{1-4}$haloalkyl. $C_{1-4}$ hydroxyalkyl, $C_{3-6}$ cycloalkyl, or $C_{3-6}$ cycloalkyl-$C_{1-4}$ alkyl is optionally substituted with 1, 2, 3, 4, or 5 substituents independently selected from H, D, oxo(C═O), —CN, —$NO_2$, —OH, —$NH_2$, —$N_3$, F, Cl, Br, or I.

In some embodiments, $R^{1a}$ is H, ethyl, ethyl-D, isopropyl, trifluoroethyl, trifluoromethyl, hydroxyethyl, cyclopropyl, or cyclopropylmethyl.

In some embodiments, Cy is

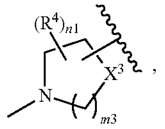

wherein $X^3$ is —NH—, or —$(CH_2)_{1-2}$—; m3 is 1, 2, or 3; and n1 is 0, 1, 2, 3, or 4.

In some embodiments, Cy is

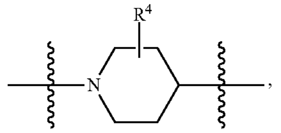

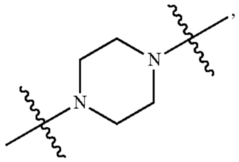

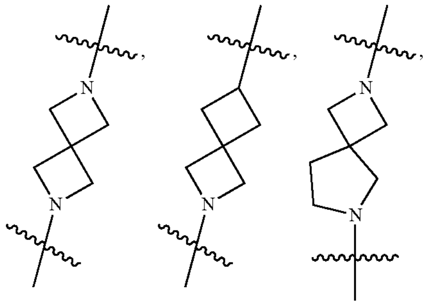

-continued

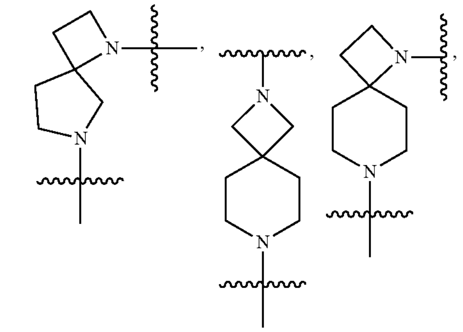

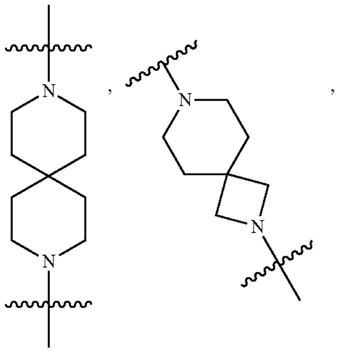

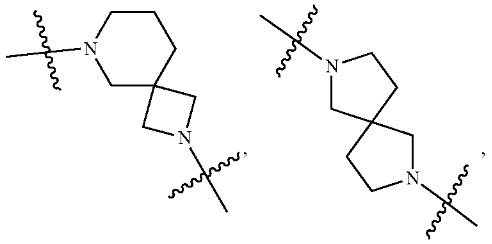

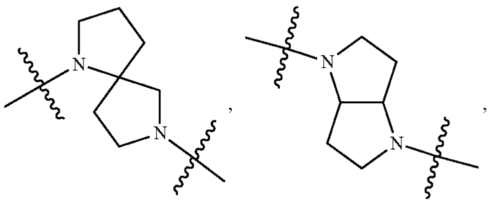

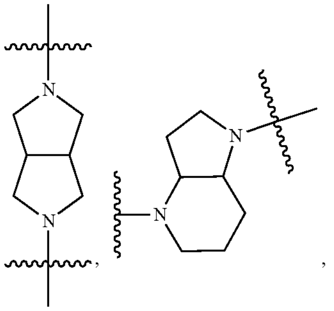

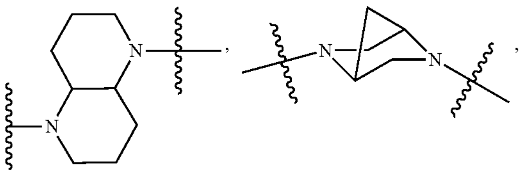

-continued

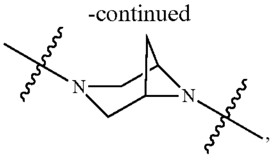
,
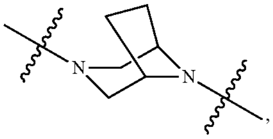
, or
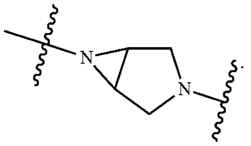
.

In some embodiments, $R^{1b}$ is H, methyl, or ethyl.

In some embodiments, Z is $C_{1-6}$ alkyl, $C_{1-6}$ haloalkyl, $C_{1-6}$ hydroxyalkyl, $C_{1-6}$ cyanoalkyl, $C_{3-6}$ heterocyclyl-$C_{1-4}$ alkyl, or $C_{3-6}$ cycloalkyl-$C_{1-4}$ alkyl, wherein each of the $C_{1-6}$ alkyl, $C_{1-6}$ haloalkyl, $C_{1-6}$ hydroxyalkyl, $C_{1-6}$ cyanoalkyl, $C_{3-6}$ heterocyclyl-$C_{1-4}$ alkyl, or $C_{3-6}$ cycloalkyl-$C_{1-4}$ alkyl is optionally substituted with one or more $R^5$; or Z is

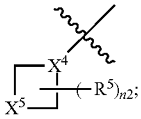
;

wherein $X^4$ is N, or —CH—;

$X^5$ is —O—, —S—, —NH—, $—(CH_2)_{m4}—NH—(CH_2)_{m5}—$, $—(CH_2)_{m4}—O—(CH_2)_{m5}—$, $—(CH_2)_{m4}—S—(CH_2)_{m5}—$, or $—(CH_2)_{m6}—$;

each of m4 is independently 1, 2, 3, or 4;

each of m5 is, independently 0, 1, 2, 3, or 4;

each of m6 is, independently 1, 2, 3, or 4; and n2 is 0, 1, 2, 3, or 4.

In some embodiments, Z is $—CH_2CH_2OH$, $—CH_2C(CH_3)_2OH$, $—CH_2C(CH_3)_2CH_2OH$, $—CH_2CH_2CN$, $—CH_2CHF_2$, $—CH(CH_3)CH_2OH$, $—C(CH_3)_2CH_2OH$, $—CH_2C(CH_3)_3$,

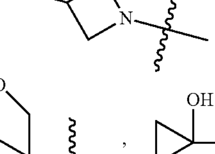
,
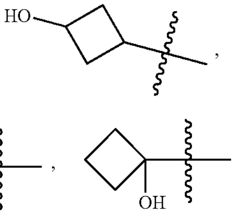
,
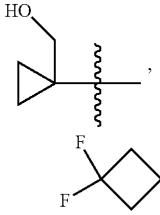
,
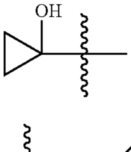
,
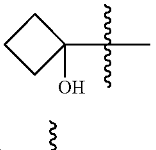
,
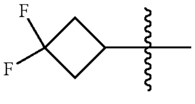
,
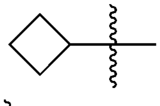
,
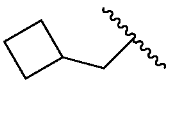
,
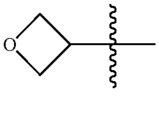
,
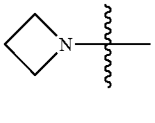
, -continued

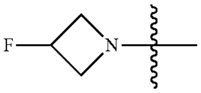
,
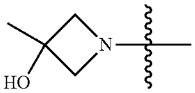
,
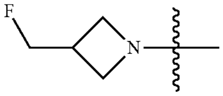
,
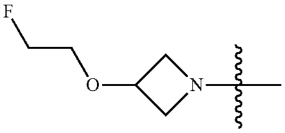
,
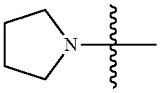
,
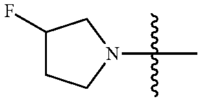
,
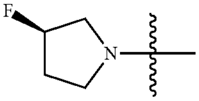
,
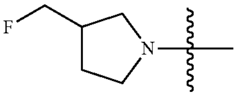
,
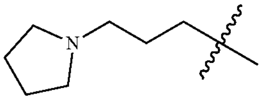
,
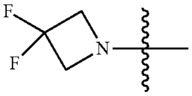
,
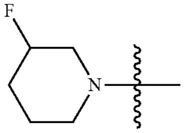
,
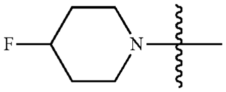
,
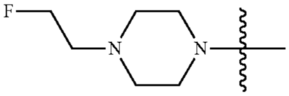
,
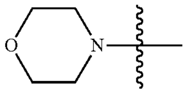
,
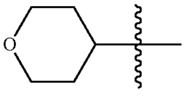
,
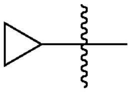
, or
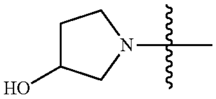
.

In some embodiments, each of $R^4$, $R^5$, $R^6$, $R^7$, and $R^8$ is, independently in each instance, H, D, oxo (C═O), —CN, $—NO_2$, —OH, $—NH_2$, $—N_3$, F, Cl, Br, I, methyl, ethyl, propyl, isopropyl, tert-butyl, methoxy, ethoxy, $—OCH_2CF$, $—OCH_2CH_2F$, $—CF_3$, $—CH_2F$, $—CH_2CF_3$, $—CH_2CH_2F$, $—CH_2CH_2CN$, $CHF_2—O—CH_2—$, $CF_3—O—CH_2—$, $—CH_2OH$, or $—CH_2CH_2OH$.

In some embodiments, the compound of the present disclosure has a structure selected from any one of the following:

(1)
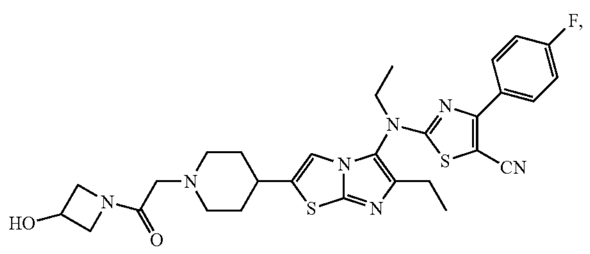
(2)
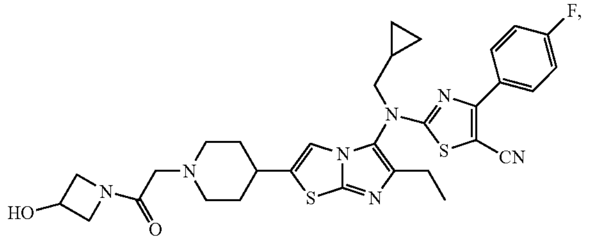
(3)
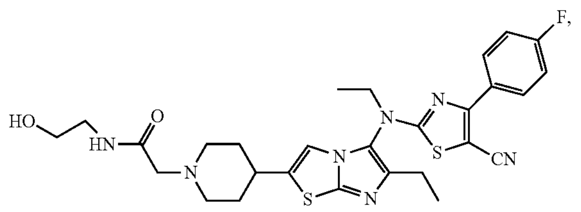
(4)
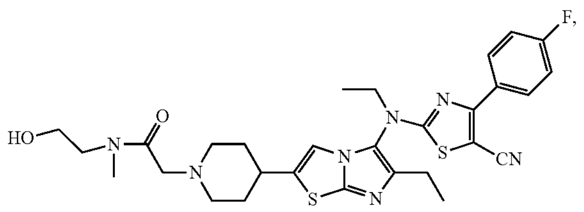
(5)
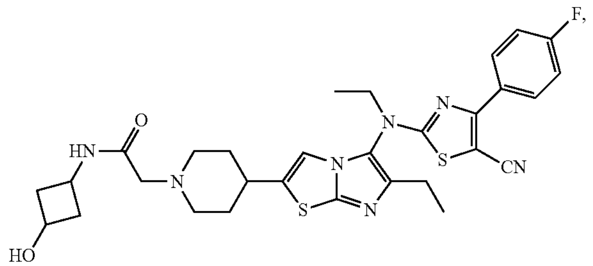
(6)
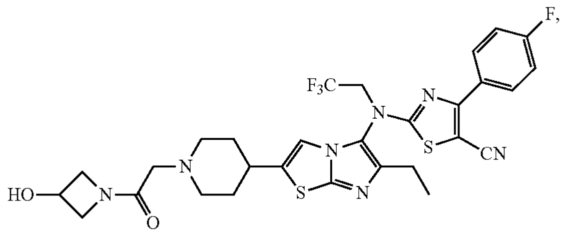
(7)
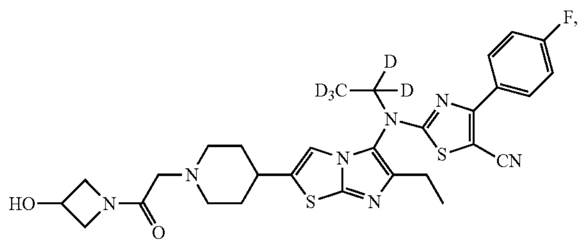
(8)
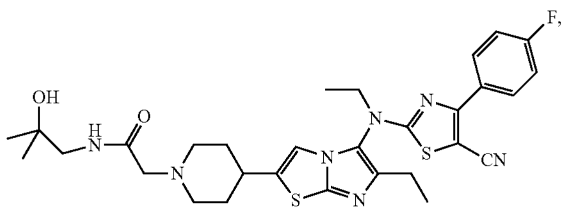
(9)
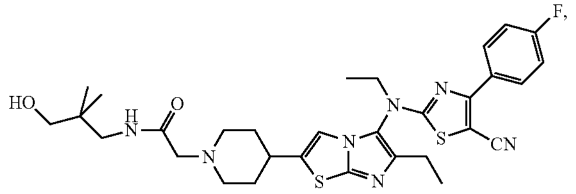
(10)
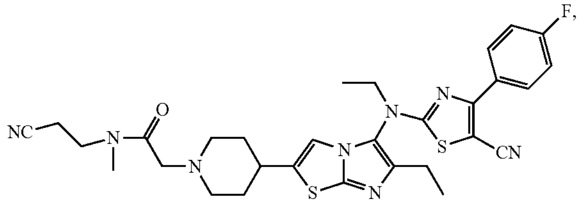
(11)
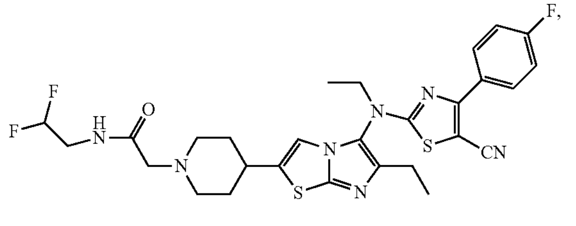
(12)
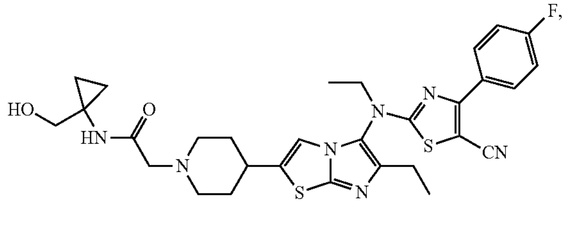

-continued
(13)
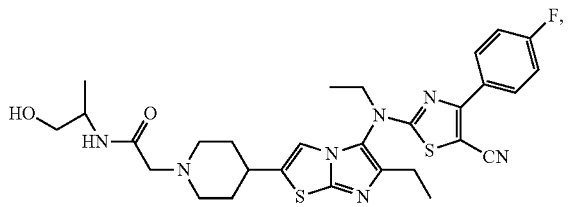
(14)
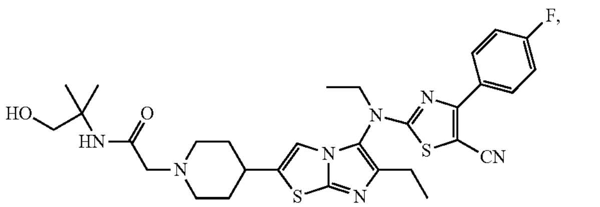
(15)
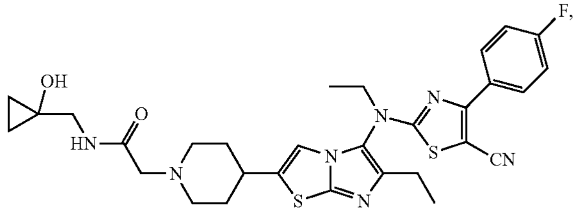
(16)
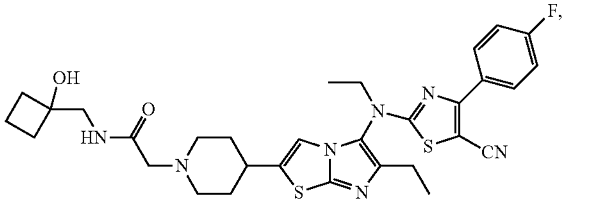
(17)
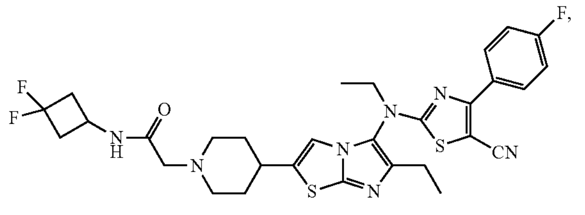
(18)
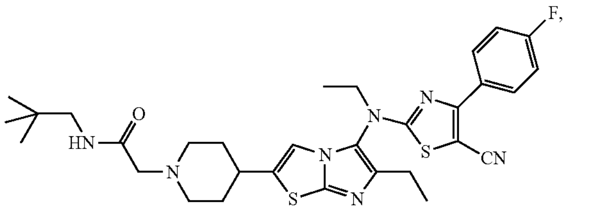
(19)
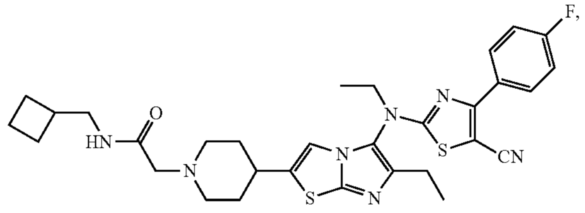
(20)
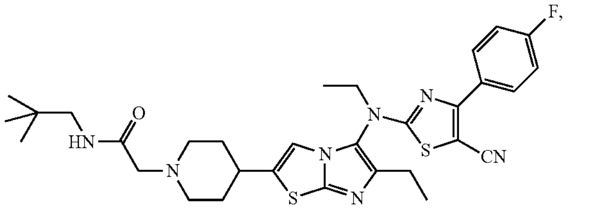
(21)
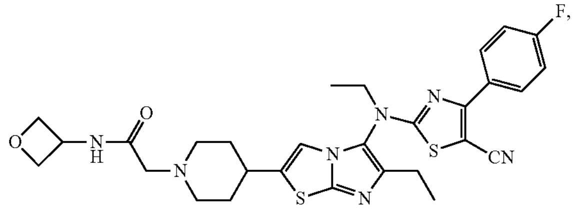
(22)
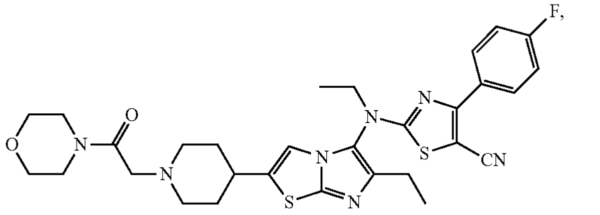
(23)
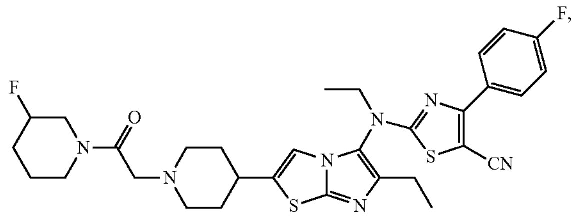
(24)
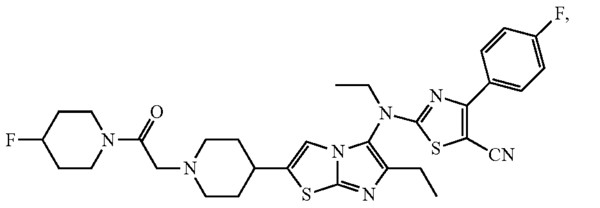
(25)
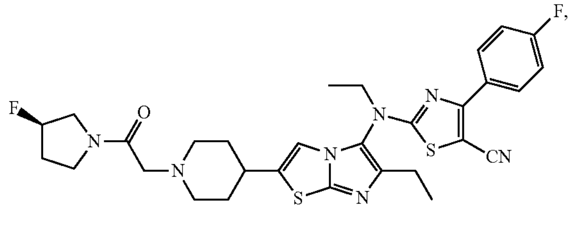

-continued
(26)
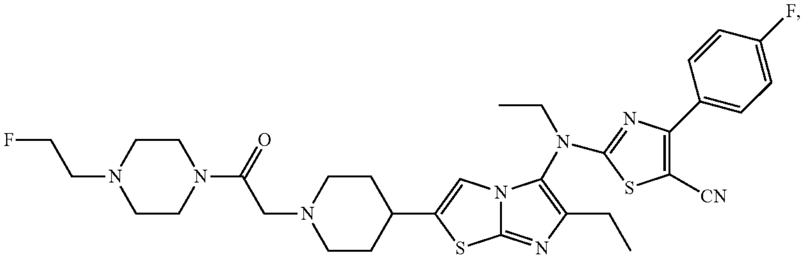
(27)
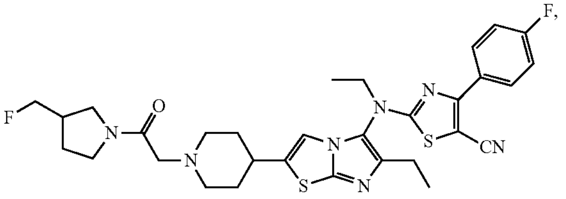
(28)
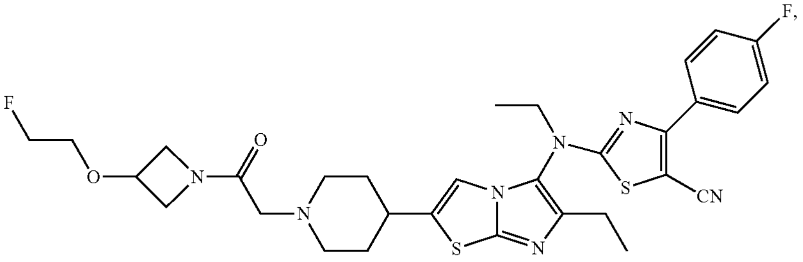
(29)
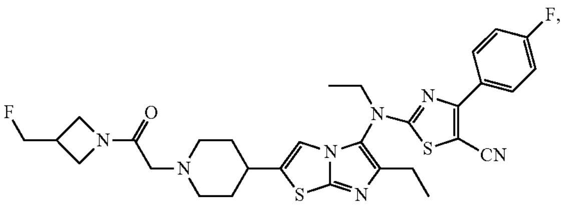
(30)
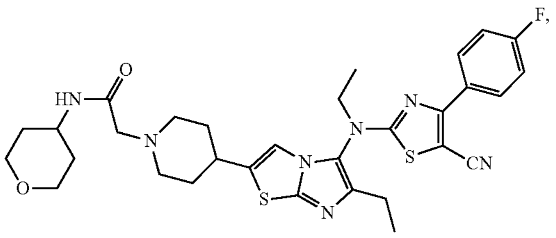
(31)
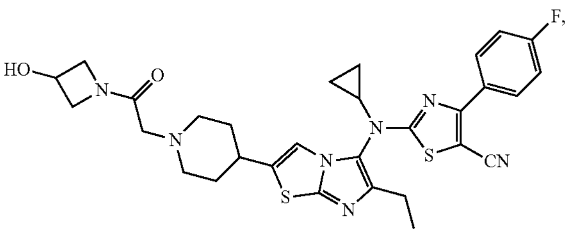
(32)
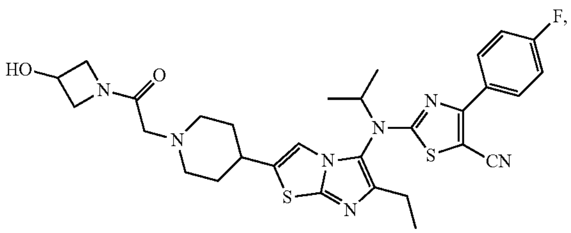
(33)
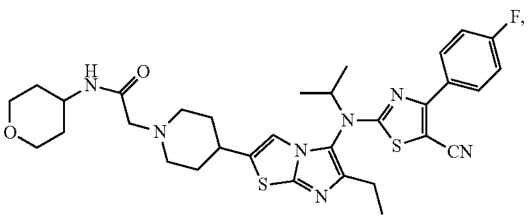
or
(34)
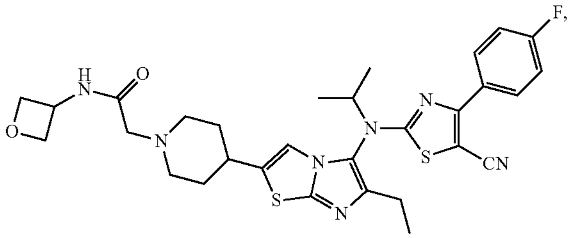

or a pharmaceutically acceptable salt, hydrate, solvate, stereoisomer, tautomer, nitrogen oxide, metabolite, prodrug, or mixture thereof.

It is another aspect to provide a pharmaceutical composition, comprising the compound of the present disclosure or a pharmaceutically acceptable salt, hydrate, solvate, stereoisomer, tautomer, nitrogen oxide, metabolite, prodrug thereof, and a pharmaceutically acceptable excipient, a diluent, or a carrier.

In some embodiments, the pharmaceutical composition of the present disclosure further comprises an additional therapeutic agent.

In some embodiments, in the pharmaceutical composition of the present disclosure, the additional therapeutic agent is a therapeutic agent for a disease in relation to fibrotic disease, proliferative disease, inflammatory disease, autoimmune disease, respiratory disease, cardiovascular disease, neurodegenerative disease, dermatologic disorder and/or abnormal vasculogenesis.

In some embodiments, in the pharmaceutical composition of the present disclosure, the additional therapeutic agent includes, but is not limited to, an immunomodulator, an analgesic, a non-steroidal anti-inflammatory drug, a steroid, a synthetic DMARDS, a proliferative disease drug, a glucocorticoid, a cytostatic agent, an alkylating agent, an anti-metabolism agent, a cytotoxic antibiotic, an antibody-based drug, etc.

It is another aspect to provide a use of the compound or the pharmaceutical composition of the present disclosure in the preparation of medicament for preventing or treating a disease with a pathological feature of Autotaxin (ATX) overexpression in a mammal.

In some embodiments, the disease with a pathological feature of Autotaxin (ATX) overexpression comprises cancer, fibrotic disease, metabolic disease, myelodysplastic syndrome, cardiovascular disease, autoimmune disease, inflammatory disease, nervous system disease, or pain.

In some embodiments, the disease with a pathological feature of Autotaxin (ATX) overexpression is idiopathic pulmonary fibrosis or hepatic fibrosis. In some embodiments, the compound or the pharmaceutical composition thereof in the present disclosure can be administrated in combination with other therapeutic agents.

In some embodiments, the use of the present disclosure comprises administrating an effective amount of the compound or the pharmaceutical composition of the present disclosure to a mammal for preventing or treating.

Pharmaceutical Composition, Preparation and Use

When the compound of the present disclosure is used as a medicament, it is usually administered in a form of a pharmaceutical composition. The composition may be prepared in a well-know manner of pharmaceutical technology and comprises at least one of the compounds according to formula I, or II of the present disclosure. In general, the compound of the present disclosure is administered in a pharmaceutically effective amount. The actual dosage of the compound of the present disclosure will usually be determined by the physician according to relevant conditions, which include symptoms to be treated, a selected administration pathway, an actual compound of the present disclosure administered, the age, weight and response of the individual patients, and symptom severity of the patients, etc.

The pharmaceutical composition of the present disclosure can be administered through various routes, including oral, rectal, transdermal, subcutaneous, intra-articular, intravenous, intramuscular, and intranasal administration, which depends on the intended delivery routes. The compound of the disclosure is prepared as an injectable or an oral composition, or as an ointment, as a lotion, or as a patch (all for transdermal administration).

The liquid compositions for oral administration may be a pharmaceutically acceptable solution, suspension, emulsion, syrup, or elixir, which contains an in tert diluent, such as water or liquid paraffin. In addition to the diluent, the above-mentioned composition may also contain some other substances, and in some embodiments, it contains a wetting agent, a sweetener, or a flavoring agent.

The compositions for parenteral administration may be emulsions or sterile solutions. In some embodiments, propylene glycol, polyethylene glycol, vegetable oil, especially olive oil, or injectable organic esters may be used as solvents or carriers; and in some embodiments, ethyl oleate may be used as a solvent or carrier. The compositions may also contain adjuvants, and in particular a wetting agent, an isotonic agent, an emulsifier, a dispensing agent and a stabilizer. Sterilization can be performed in several ways, in some embodiments, for example by using a bacteriological filter, by radiation or by heating. They may also be prepared in the form of sterile solid compositions, which may be dissolved in sterile water or any other injectable sterile medium at the time of use.

The composition may also be an aerosol. For use in a liquid aerosol form, the composition may be a stable sterile solution or a solid composition dissolved in heat-free sterile water, saline, or any other pharmaceutically acceptable carrier during use. For use in a dry aerosol form intended for direct inhalation, the active ingredient is finely separated and combined with a water-soluble solid diluter or carrier and, in some embodiments, combined with glucan, mannitol or lactose.

Typical pharmaceutical compositions and dosage forms contain one or more excipients. Suitable excipients are known to one skilled in the pharmaceutical field. In some embodiments, suitable excipients include starch, glucose, lactose, sucrose, gelatin, malt, rice, flour, chalk, silica gel, sodium stearate, glycerin monostearate, talc, sodium chloride, skimmed milk powder, glycerin, propylene, ethylene glycol, water, ethanol, etc. Whether a particular excipient is suitable for incorporation into a pharmaceutical composition or dosage forms depends on many factors well-known in the art, including, but not limited to, the way that the dosage form is administered to the subject, and the specific active ingredients in the dosage. If necessary, the composition or single unit dosage form also contain a little amount of wetting agent, emulgator, or pH buffering agent.

In another aspect, the present disclosure provides a compound of the present disclosure or a pharmaceutical composition including the compound of the present disclosure, for medical use. In specific embodiments, the present disclosure provides a compound of the present disclosure or a pharmaceutical composition including the compound of the present disclosure for preventing and/or treating a disease in relation to fibrotic disease, proliferative disease, inflammatory disease, autoimmune disease, respiratory disease, cardiovascular disease, neurodegenerative disease, dermatologic disorder and/or abnormal vasculogenesis.

In some embodiments, the present disclosure provides a compound of the present disclosure or a pharmaceutical composition including the compound of the present disclosure for use in preparation of a medicament for preventing and/or treating a disease in relation to fibrotic disease, proliferative disease, inflammatory disease, autoimmune disease, respiratory disease, cardiovascular disease, neurodegenerative disease, dermatologic disorder and/or abnormal vasculogenesis.

In some embodiments, the present disclosure provides a compound of the present disclosure or a pharmaceutical composition including the compound of the present disclosure. In specific embodiments, other therapeutic agents are the therapeutic agents for a disease in relation to fibrotic disease, proliferative disease, inflammatory disease, autoimmune disease, respiratory disease, cardiovascular disease, neurodegenerative disease, dermatologic disorder and/or abnormal vasculogenesis.

In some embodiments, the present disclosure provides a compound of the present disclosure or a pharmaceutical composition comprising the compound of the present disclosure for preventing and/or treating fibrotic diseases. In a specific embodiment, the fibrotic disease is selected from the group consisting of idiopathic pulmonary fibrosis (IPF), cystic fibrosis, other diffuse parenchymal lung disease of different etiologies (including iatrogenic drug-induced fibrosis, occupational and/or environment-induced fibrosis), granulomatous disease (sarcoidosis, allergic pneumonia), collagen vascular disease, alveolar protein deposition, Langerhans cell granuloma, lymphangiomyotysis, genetic disease (Hermans Chi-Pudlak syndrome, tuberous sclerosis, neurofibroma, metabolic accumulation disorder, familial interstitial lung disease), radiation-induced fibrosis, chronic obstructive pulmonary disease (COPD), *scleroderma*, Bleomycin-induced pulmonary fibrosis, chronic asthma, silicosis, asbestos-induced pulmonary fibrosis, acute respiratory distress syndrome (ARDS), renal fibrosis, renal tubule interstitial fibrosis, glomerulonephritis, localized segment glomerulosclerosis, IgA nephropathy, hypertension, Alport's disease (Alport), intestinal fibrosis, liver fibrosis, cirrhosis, alcohol-induced liver fibrosis, toxin/drug-induced liver fibrosis, hemochromatosis, non-alcoholic steatohepatitis (NASH), bile duct damage, primary biliary cirrhosis, infection-induced liver fibrosis, virus-induced liver fibrosis and autoimmune hepatitis, corneal scar, hypertrophic scar, Dupuytren disease, scar pimple, skin fibrosis, skin *scleroderma*, systemic sclerosis, spinal cord injury/fibrosis, bone marrow fibrosis, vascular restenosis, atherosclerosis, arteriosclerosis, Wegener's granulomatosis, Peyronie's disease or chronic lymphocytic. More specifically, the fibrotic disease is idiopathic pulmonary fibrosis (IPF).

In some other embodiments, the present disclosure provides a compound of the present disclosure or a pharmaceutical composition comprising the compound of the present disclosure, which is used for preparing a medicament in preventing and/or treating fibrotic diseases. In a specific embodiment, the fibrotic disease is selected from the group consisting of idiopathic pulmonary fibrosis (IPF), cystic fibrosis, other diffuse parenchymal lung disease of different etiologies (including iatrogenic drug-induced fibrosis, occupational and/or environment-induced fibrosis), granulomatous disease (sarcoidosis, allergic pneumonia), collagen vascular disease, alveolar protein deposition, Langerhans cell granuloma, lymphangiomyotysis, genetic disease (Hermans Chi-Pudlak syndrome, tuberous sclerosis, neurofibroma, metabolic accumulation disorder, familial interstitial lung disease), radiation-induced fibrosis, chronic obstructive pulmonary disease (COPD), *scleroderma*, Bleomycin-induced pulmonary fibrosis, chronic asthma, silicosis, asbestos-induced pulmonary fibrosis, acute respiratory distress syndrome (ARDS), renal fibrosis, renal tubule interstitial fibrosis, glomerulonephritis, localized segment glomerulosclerosis, IgA nephropathy, hypertension, Alport's disease (Alport), intestinal fibrosis, liver fibrosis, cirrhosis, alcohol-induced liver fibrosis, toxin/drug-induced liver fibrosis, hemochromatosis, non-alcoholic steatohepatitis (NASH), bile duct damage, primary biliary cirrhosis, infection-induced liver fibrosis, virus-induced liver fibrosis and autoimmune hepatitis, corneal scar, hypertrophic scar, Dupuytren disease, scar pimple, skin fibrosis, skin *scleroderma*, systemic sclerosis, spinal cord injury/fibrosis, bone marrow fibrosis, vascular restenosis, atherosclerosis, arteriosclerosis, Wegener's granulomatosis, Peyronie's disease or chronic lymphocytic. More specifically, the fibrotic disease is idiopathic pulmonary fibrosis (IPF).

In another method for treatment, the present disclosure provides a method of preventing and/or treating mammal with a fibrotic disease, the method comprises administrating an effective amount of one or more compounds or the pharmaceutical compositions of the present disclosure for preventing and/or treating the disease. In a specific embodiment, the fibrotic disease is selected from the group consisting of idiopathic pulmonary fibrosis (IPF), cystic fibrosis, other diffuse parenchymal lung disease of different etiologies (including iatrogenic drug-induced fibrosis, occupational and/or environment-induced fibrosis), granulomatous disease (sarcoidosis, allergic pneumonia), collagen vascular disease, alveolar protein deposition, Langerhans cell granuloma, lymphangiomyotysis, genetic disease (Hermans Chi-Pudlak syndrome, tuberous sclerosis, neurofibroma, metabolic accumulation disorder, familial interstitial lung disease), *scleroderma*, Bleomycin-induced pulmonary fibrosis, chronic asthma, silicosis, asbestos-induced pulmonary fibrosis, acute respiratory distress syndrome (ARDS), renal fibrosis, renal tubule interstitial fibrosis, glomerulonephritis, localized segment glomerulosclerosis. IgA nephropathy, hypertension, Alport's disease (Alport), intestinal fibrosis, liver fibrosis, cirrhosis, alcohol-induced liver fibrosis, toxin/drug-induced liver fibrosis, hemochromatosis, non-alcoholic steatohepatitis (NASH), bile duct damage, primary biliary cirrhosis, infection-induced liver fibrosis, virus-induced liver fibrosis and autoimmune hepatitis, corneal scar, hypertrophic scar, Dupuytren disease, scar pimple, skin fibrosis, skin *scleroderma*, systemic sclerosis, spinal cord injury/fibrosis, bone marrow fibrosis, vascular restenosis, atherosclerosis, arteriosclerosis, Wegener's granulomatosis, Peyronie's disease or chronic lymphocytic. More specifically, the fibrotic disease is idiopathic pulmonary fibrosis (IPF).

A particular scheme of the method of the present disclosure includes administering an effective amount of the compound having a formula I, Ia, II, or IIa of the present disclosure to an individual suffering from a fibrotic disease for a period, which is sufficient to reduce the level of fibrosis in the individual, and to terminate the process that causes the fibrosis. A specific embodiment of the method includes administering an effective amount of a compound having a formula I, Ia, II, or IIa of the present disclosure to an individual patient suffering from developing idiopathic pulmonary fibrosis for a period, which is sufficient to reduce or prevent idiopathic pulmonary fibrosis in the patient, and to terminate the process causing the idiopathic pulmonary fibrosis.

It is apparent for one skilled in the art that co-administration includes delivering two or more therapeutic agents in any forms to patients as part of the same treatment regimen. Although the two or more active agents can be simultaneously administrated in a single preparation (i.e., as a single pharmaceutical composition), this is not necessary. The active agents can be also administrated in different preparation at different times.

In order to describe the present disclosure, embodiments are listed hereinafter. It should be understood that the present disclosure is not limited to the embodiments, and only provides methods for practicing the present disclosure.

In general, unless otherwise stated, the compound of the present disclosure can be prepared by the method described herein, wherein the substituents are defined as shown in formulas I, or II. The following reaction schemes and embodiments are used to further illustrate the content of the present disclosure.

It should be recognized by one skilled in the conventional art that the chemical reactions described in the present disclosure can be used to appropriately prepare many other compounds of the present disclosure, and other methods for preparing the compounds are considered to be within the scope of the present disclosure. For example, the synthesis of non-exemplary compounds according to the present disclosure may be successfully prepared by one skilled in the art through modifying methods, such as appropriate protection of interfering groups, by using other well-known reagents in addition to those described in the present disclosure, or regularly modifying some reaction conditions. In addition, the reaction disclosed in the present disclosure or well-known reaction conditions are also recognized to be applicable for the preparation of other compounds of the present disclosure.

In the embodiments described hereinafter, unless otherwise indicated, all the temperatures are set to degree centigrade. The reagents are commercially available from commercial suppliers, such as Aldrich Chemical Company, Arco Chemical Company, Energy-chemical Company, Shanghai Shaoyuan Company, J&K Chemical Company, Aladdin Chemical Company, Meryer Chemical Company, TCI Chemical Company, Xiya Reagent Company, Bidepharm Company, Macklin Company, and Alfa Chemical Company, and are used without further purifying, unless otherwise indicated. General reagents are purchased from Shantou Xilong Chemical Co., Ltd, Guangdong Guanghua Sci-Tech Co., Ltd., Guangzhou Chemical Reagent Factory, Tianjin Haoyuyu Chemicals Co., Ltd., Tianjin Fuchen Chemical Reagent Factory, Wuhan Xinhuayuan Science and Technology Development Co., Ltd., Qingdao Tenglong Chemical Reagent Co., Ltd., and Qingdao Haiyang Chemical Factory.

Anhydrous tetrahydrofuran, dioxane, methylbenzene, and diethyl ether are obtained by refluxing and drying with metallic sodium. Anhydrous dichloromethane and chloroform are obtained by refluxing and drying with calcium hydride. Ethyl acetate, petroleum ether, n-hexane, N, N'-dimethylacetamide, and N, N'-dimethylformamide are dried with anhydrous sodium sulfate before use.

The following reactions generally perform under a positive pressure of nitrogen gas or argon gas or with a drying tube on anhydrous solvent (unless otherwise indicated). Reaction flasks are plugged with suitable rubber plugs, and substrates are injected by a syringe. Glasswares are all dried.

Chromatographic column uses silica gel. The silica gel (300 to 400 meshes) is purchased from Qingdao Haiyang Chemical Factory.

$^1H$ NMR spectrum is recorded by Bruker 400 MHz or 600 MHz nuclear magnetic resonance spectrometer. $^1H$ NMR spectrum uses $CDCl_3$, DMSO-$d_6$, $CD_3OD$, or acetone-$d_6$ as solvent (in ppm), and uses TMS (0 ppm) or chloroform (7.26 ppm) as reference. When multiplicities are present, the following abbreviations are used: s (singlet), d (double), t (triplet), m (multiplet), br (broadened), dd (doublet of doublets), dt (doublet of triplets). Coupling constants are used in Hz.

The measurement conditions of low-resolution mass spectrometer (MS) data are: Agilent 6120 quadrupole HPLC-M (column model: Zorbax SB-C18, 2.1×30 mm, 3.5 microns, 6 min, flow rate: 0.6 mL/min. The mobile phase: 5%-95% (the ratio of (0.1% formic acid in $CH_3CN$) to (0.1% formic acid in $H_2O$)), being ionized by electrospray ionization (ESI), and detected by UV at 210 nm/254 nm.

Pure compounds are prepared by Agilent 1260 pre-HPLC or Calesep pump 250 pre-HPLC (column model: NOVASEP 50/80 mm DAC) and are detected by UV at 210 nm/254 nm.

The typical synthetic steps for preparing the compounds disclosed in the present disclosure are shown as the following Synthetic Scheme 1.

Synthetic Scheme 1

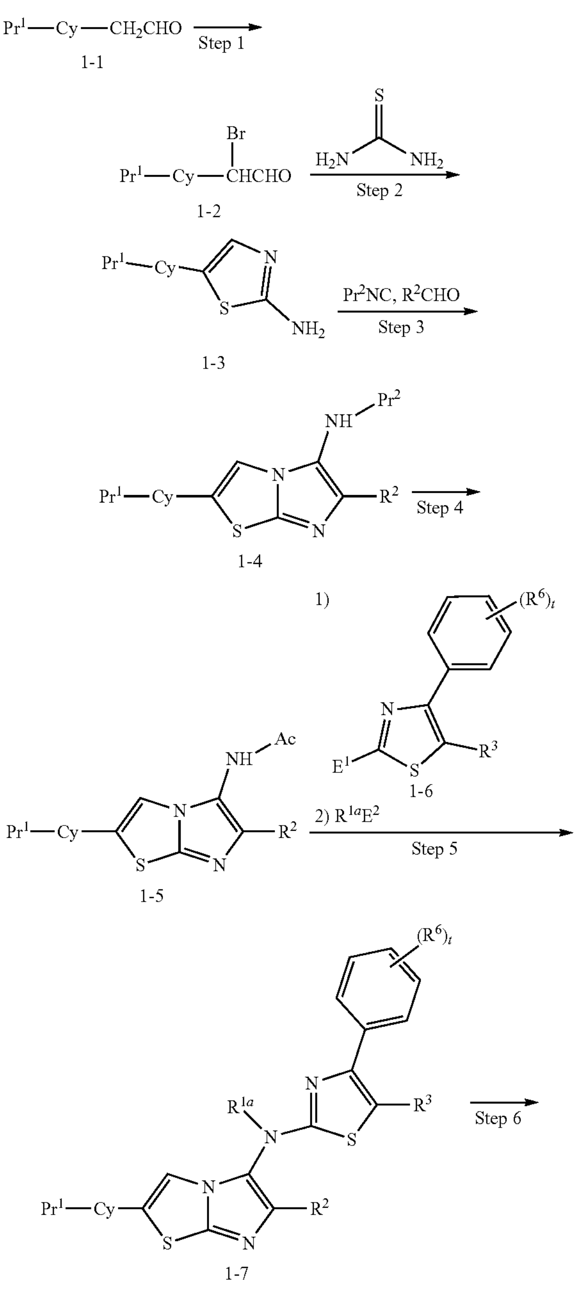

-continued

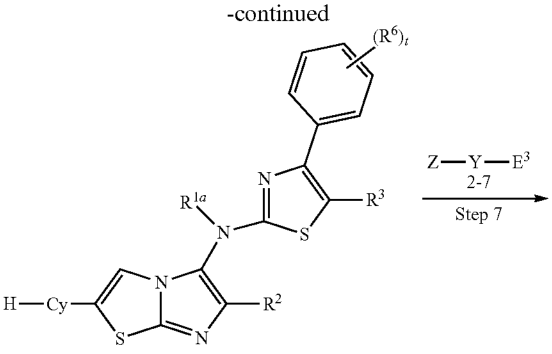

1-8

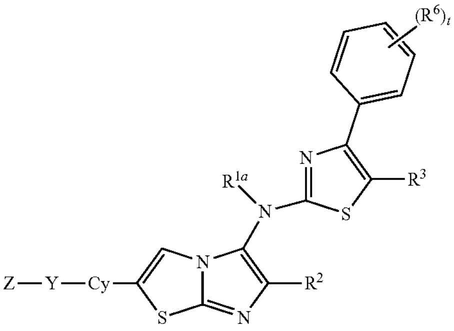

1-9 wherein, $E^1$ is selected from Cl, Br, or I; $E^2$ is selected from Cl, Br, I, or $B(OH)_2$; $E^3$ is selected from Cl, Br, I, OMs, OTs or OTf; $Pr^1$ is selected from Boc, Cbz, or PMB; $Pr^2$ is selected from tert-butyl, or 2,4,4,-trimethylpent-2-yl; $R^{1a}$, $R^2$, $R^3$, $R^6$, Y, Z, Cy, and t have the definitions described in the present disclosure.

Intermediate 1-1 is reacted with NBS or phenyltrimethylammonium bromide to obtain an intermediate 1-2; the intermediate 1-2 is reacted with thiourea through a ring-closing reaction, to obtain an intermediate 1-3: the intermediate 1-3 is reacted with $Pr^2NC$ and aldehyde ($R^2CHO$) through a three-component reaction in the presence of Lewis acid, to obtain an intermediate 1-4, and the intermediate 1-4 is reacted with acetic acid under heating conditions to obtain an intermediate, which is further reacted with Boc anhydride or CbzCl to obtain an intermediate 1-5; the intermediate 1-5 is firstly reacted with strong alkali to obtain an intermediate, which is further reacted with an intermediate 1-6 through a nucleophilic substitution reaction, and then reacted with a substituted alkyl $R^{1a}E^2$ to obtain an intermediate 1-7; the intermediate 1-7 can be reacted in acid conditions, or be hydrogenated by palladium catalyst, or be reacted with trimethyliodosilane to remove the protection group of $Pr^1$, so as to obtain an intermediate 1-8; the intermediate 1-8 is reacted with an intermediate 2-7 in the presence of alkali under a heating condition, through a nucleophilic substitution reaction to obtain a compound of formula 1-9.

EMBODIMENTS

Embodiment 1

Preparation of 2-(ethyl(6-ethyl-2-(1-(2-(3-hydroxyazetidin-1-yl)-2-oxoethyl)piperidin-4-yl) imidazo[2,1-b]thiazol-5-yl)amino)-4-(4-fluorophenyl) thiazole-5-carbonitrile

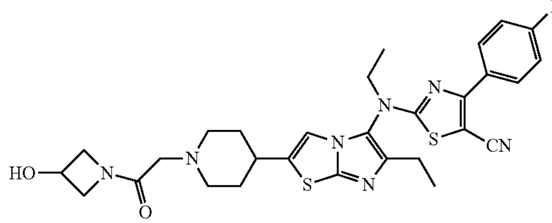

STEP 1) benzyl 4-(hydroxyethyl)piperidine-1-carboxylate

Triethylamine (1.08 mL, 7.76 mmol) was added to a solution of 2-(piperidin-4-yl)ethanol (0.5 g, 3.88 mmol) in dichloromethane (10 mL). After the mixture was cooled to 0° C., benzyl chloroformate (0.6 mL, 4.26 mmol) was dripped into the mixture. The reaction mixture was stirred for 2 hours at 0° C., and then it was concentrated under reduced pressure to remove solvent. Subsequently, water (20 mL) was added to the reaction liquid, and the liquid was extracted by ethyl acetate (20 mL×3). The organic phases were combined, washed by saturated saline, dried by anhydrous sodium sulfate, and concentrated under reduced pressure to obtain 0.8 g of a crude product, which was directly used for the next reaction.

STEP 2): benzyl 4-(oxoethyl)piperidinyl-1-carboxylate

Dimethylsulfoxide (0.8 mL, 11.2 mmol) was dripped into a solution of oxalyl chloride (0.48 mL, 5.67 mmol) in dichloromethane (5 mL) under the argon protection at −70° C. After the mixture was stirred for 30 min, a solution of benzyl 4-(hydroxyethyl)piperidine-1-carboxylate (0.8 g, 3.04 mmol) in dicloromethane (8 mL) was dripped, and triethylamine (2.3 mL, 16.6 mmol) was added. After the mixture was stirred for 1 hour, it was concentrated under reduced pressure to remove solvent. Subsequently, water (20 mL) was added to the mixture, and the mixture was extracted by ethyl acetate (20 mL×3). The organic phases were combined, washed by saturated saline, dried by anhydrous sodium sulfate, and concentrated under reduced pressure to obtain residues, which was further purified through a column chromatography (petroleum ether:ethyl acetate=10:1) to obtain a light yellow oily product, i.e., benzyl 4-(oxoethyl)piperidinyl-1-carboxylate (0.57 g, 72%). LCMS $[M+1]^+$: 262.1.

STEP 3) benzyl 4-(1-bromo-2-oxoethyl)piperidine-1-carboxylate

Trimethylphenylammonium tribromide (0.94 g, 2.5 mmol) was added to a solution of benzyl 4-(oxoethyl) piperidine-1-carboxylate (0.57 g, 2.18 mmol) in tetrahydrofuran (5 mL) at 0° C. After the mixture was stirred for 50 min at 0° C., it was concentrated under reduced pressure. Subsequently, water (15 mL) was added to the residues, and the mixture was extracted by ethyl acetate (15 mL×3). The organic phases were combined, washed by saturated saline, dried by anhydrous sodium sulfate, and concentrated under resued pressure to obtain a light yellow oily product, i.e., benzyl 4-(1-bromo-2-oxoethyl)piperidine-1-carboxylate (714 mg), which was directly used for the next reaction.

STEP 4): benzyl 4-(2-aminothiazol-5-yl)piperidine-1-carboxylate

Thiourea (0.33 g, 4.4 mmol) was added to a solution of benzyl 4-(1-bromo-2-oxoethyl)piperidine-1-carboxylate (710 mg, 2.09 mmol) in absolute ethanol (12 mL) solution. The mixture was reacted for 2 hours at 80° C. and then the reaction was completed. After the reaction liquid was cooled to room temperature, the liquid was concentrated under reduced pressure. Water (30 mL) was added to the liquid, and the liquid was extracted by ethyl acetate (20 mL×3). Subsequently, the organic phases were combined, washed by saturated sodium bicarbonate solution, dried by anhydrous sodium sulfate, and concentrated under reduced pressure to obtain residues, which were purified through a column chromatography (petroleum ether:ethyl acetate=2:1) to obtain a product (0.54 g, 81%). LCMS $[M+1]^+$: 318.1

STEP 5): benzyl 4-(5-(tert-butylamino)-6-ethylimidazo[2,1-b]thiazol-2-yl)piperidine-1-carboxylate Tert-butyl isocyanide (0.17 g, 2 mmol), n-propanal (0.1 g, 3.4 mmol), and magnesium chloride (10 mg, 0.08 mmol) were successively added to a solution of benzyl 4-(2-aminothiazol- 5-yl)piperidine-1-carboxylate (0.54 g, 1.7 mmol) in glycol dimethyl ether (15 mL) at 0° C. The mixture was stirred for 10 min, and after the temperature was increased to room temperature, the mixture was further stirred for 2 hours. The reaction liquid was filtered, and it was concentrated under reduced pressure to obtain a crude product (0.5 g). LCMS $[M+1]^+$: 441.2.

STEP 6): tert-butyl 4-(5-acetamido-6-ethylimidazo[2,1-b]thiazol-2-yl)piperidine-1-carboxylate Para-toluenesulfonic acid (0.22 g, 1.14 mmol) was added to a solution of benzyl 4-(5-(tert-butylamino)-6-ethylimidazo[2,1-b]thiazol-2-yl)piperidine-1-carboxylate (0.5 g, 1.14 mmol) in acetic acid (5 mL), and the mixture was reacted overnight at 100° C. After the reaction liquid was cooled, it was concentrated under reduced pressure. Acetic acetate (15 mL) and water (15 mL) were added to the mixture for separating aqueous phase. Dioxane (10 mL), triethylamine (0.79 mL, 5.7 mmol), and di-tert-butyl pyrocarbonate (0.39 mL, 1.71 mmol) were added to the aqueous phase and stirred for 3 hours at room temperature. The reaction liquid was concentrated under reduced pressure to obtain residues. Water (20 mL) was added to the residues, and the residues were extracted by ethyl acetate (15 mL×3). Subsequently, the organic phases were combined, washed by saturated saline, dried by anhydrous sodium sulfate, and purified through a column chromatography (petroleum ether:ethyl acetate=1:1) to obtain a product (0.2 g, 45%). LCMS $[M+1]^+$: 393.2

STEP 7): tert-butyl 4-(5-((5-cyano-4-(4-fluorophenyl)thiazole-2-yl)(ethyl)amino)-6-ethylimidazo[2,1-b]thiazol-2-yl)piperidine-1-carboxylate 60% of NaH (46 mg, 1.14 mmol) was added to a solution of tert-butyl 4-(5-acetamido-6-ethylimidazo[2,1-b]thiazol-2-yl)piperidine-1-carboxylate (150 mg, 0.38 mmol) in tetrahydrofuran (6 mL) in an ice-bath under argon protection, and the mixture was stirred for 15 min. A solution of 2-chloro-4-(4-fluorophenyl)thiazole-5-carbonitrile (91 mg, 0.38 mmol) in tetrahydrofuran (3 mL) was gradually dripped. After the temperature of the mixture was increased to room temperature, the mixture was reacted for 30 min. Thin layer Chromatography (TLC) plates showed that the reaction was completed. Iodomethane (89 mg, 0.57 mmol) was added to the reaction liquid, and the mixture was continued to react for 3 hours. LC-MS detection showed that the reaction was completed. Subsequently, the reaction liquid was poured into water (20 mL), and the liquid was extracted by ethyl acetate (15 mL×3). The organic phases were combined, washed by saturated saline, dried by anhydrous sodium sulfate, and concentrated under reduced pressure. The residues were purified through a column chromatography (petroleum ether:ethyl acetate=3:1) to obtain a white solid product, i.e., tert-butyl 4-(5-((5-cyano-4-(4-fluorophenyl)thiazole-2-yl)(ethyl)amino)- 6-ethylimidazo[2,1-b]thiazol-2-yl)piperidine-1-carboxylate (137 mg, 62%). LCMS [M+1]: 581.2.

STEP 8): 2-((6-ethyl-2-(piperidin-4-yl)imidazo[2,1-b]thiazol-5-yl)(ethyl)amino)-4-(4-fluorophenyl)thiazole-5-carbonitrile Trifluoroacetic acid (0.5 mL) was added to a solution of tert-butyl 4-(5-((5-cyano-4-(4-fluorophenyl)thiazole-2-yl)(ethyl)amino)-6-ethylimidazo[2,1-b]thiazol-2-yl)piperidine-1-carboxylate (137 mg, 0.24 mmol) in dichloromethane (3 mL), and the mixture was stirred at room temperature and reacted for 3 hours. LC-MS detection showed that the reaction was completed. The reaction liquid was concentrated under reduced pressure, and the residues were dissolved in methanol (6 mL). $NaHCO_3$ (50 mg) was added to neutralize the reaction liquid under stirring for 30 min. Subsequently, the liquid was concentrated under reduced pressure, and residues were dissolved after dichloromethane (10 mL) was added. The liquid was filtered and concentrated under reduced pressure to obtain a white solid product, i.e., 2-((6-ethyl-2-(piperidin-4-yl)imidazo[2,1-b]thiazol-5-yl)(ethyl)amino)-4-(4-fluorophenyl)thiazole-5-carbonitrile (112 mg, 89%). MS (m/z): 481.2 [M+1]

STEP 9): 2-(ethyl(6-ethyl-2-(1-(2-(3-hydroxyazetidin-1-yl)-2-oxoethyl)piperidin-4-yl) imidazo[2,1-b]thiazol-5-yl)amino)-4-(4-fluorophenyl)thiazole-5-carbonitrile $K_2CO_3$ (96 mg, 0.70 mmol), KI (19 mg, 0.12 mmol), and 2-chloro-1-(3-hydroxyazetidin-1-yl)aceton (35 mg, 0.23 mmol) was added to a solution of 2-((6-ethyl-2-(piperidin-4-yl)imidazo[2,1-b]thiazol-5-yl)(ethyl)amino)-4(4-fluorophenyl)thiazole carbonitrile (112 mg, 0.23 mmol) in acetonitrile (3 mL). After the mixture was increased to 65° C., the mixture was reacted for 5 hours. LC-MS detection showed that the reaction was completed. Subsequently, the liquid was filtered and concentrated under reduced pressure. The residues were purified by thick preparative plates (dichloromethane:methanol=20:1) to obtain a white solid product, i.e., 2-(ethyl(6-ethyl-2-(1-(2-(3-hydroxyazetidin-1-yl)-2-oxoethyl)piperidin-4-yl)imidazo[2,1-b]thiazol-5-yl)amino)-4-(4-fluorophenyl)thiazole-5-carbonitrile (66 mg, 48%). $^1H$ NMR (400 MHz, $CDCl_3$) δ: 8.13 (m, 2H), 7.16 (m, 2H), 6.94 (m, 1H), 4.68 (m, 1H), 4.44 (m, 1H), 4.28 (m, 1H), 4.11

(m, 2H), 3.94 (m, 2H), 3.21 (m, 4H), 2.76 (m, 1H), 2.60 (m, 2H), 2.47 (m, 2H), 2.04 (m, 2H), 1.31 (m, 6H), 1.25 (s, 3H). LCMS $[M+1]^+$: 594.2.

Embodiment 2

Preparation of 2-(cyclopropylmethyl(6-ethyl-2-(1-(2-(3-hydroxyazetidin-1-yl)-2-oxoethyl) piperidin-4-yl) imidazo[2,1-b] thiazol-5-yl) amino)-4-(4-fluorophenyl) thiazole-5-carbonitrile

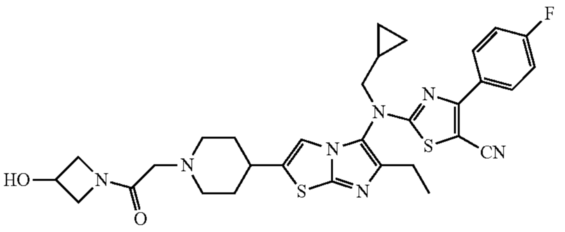 [SMILES: CCc1nc2sc(C3CCN(CC(=O)N4CC(O)C4)CC3)cn2c1N(CC1CC1)c1nc(-c2ccc(F)cc2)c(C#N)s1]

The title compound of Embodiment 2 was synthesized referring to the synthesis steps of Embodiment 1, apart from the fact that bromomethylcyclopropane was used to replace iodoethane, and therefore a white solid product, i.e., 2-(cyclopropylmethyl(6-ethyl-2-(1-(2-(3-hydroxyazetidin-1-yl)-2-oxoethyl)piperidin-4-yl)imidazo[2,1-b]thiazol-5-yl)amino)-4-(4-fluorophenyl)thiazole-5-carbonitrile (51 mg, 34%) was obtained. $^1$H NMR (400 MHz, $CDCl_3$) δ: 8.12 (m, 2H), 7.16 (m, 2H), 7.00 (m, 1H), 4.68 (m, 1H), 4.44 (m, 1H), 4.27 (m, 1H), 4.12 (m, 1H), 3.98 (m, 1H), 3.90 (m, 1H), 3.69 (m, 1H), 3.20 (m, 4H), 2.78 (m, 1H), 2.64-2.53 (m, 4H), 2.04 (m, 2H), 1.31 (m, 3H), 1.25 (s, 3H), 1.14 (m, 1H), 0.54 (m, 2H), 0.33 (m, 1H), 0.23 (m, 1H). LCMS $[M+1]^+$: 620.2.

Embodiment 3

Preparation of 2-(4-(5-((5-cyano-4-(4-fluorophenyl) thiazol-2-yl)(ethyl)amino)-6-ethylimidazo[2,1-b] thiazol-2-yl]piperidin-1-yl)-N-(2-hydroxyethyl)acetamide

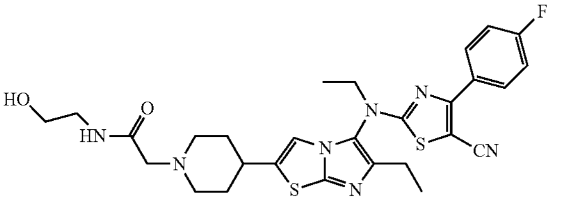 [SMILES: CCc1nc2sc(C3CCN(CC(=O)NCCO)CC3)cn2c1N(CC)c1nc(-c2ccc(F)cc2)c(C#N)s1]

STEP 1) ethyl 2-(4-(5-((5-cyano-4-(4-fluorophenyl)thiazol-2-yl)(ethyl)amino)-6-ethylimidazo[2,1-b] thiazol-2-yl) piperidin-1-yl)acetate Potassium carbonate (2.42 g, 17.5 mmol) was added to a solution of 2-((6-ethyl-2-(piperidin-4-yl)imidazo[2,1-b]thiazol-5-yl)(ethyl)amino)-4-(4-fluorophenyl)thiazole-5-carbonitrile (2.8 g, 5.83 mmol) in acetonitrile (25 mL). The mixture was cooled in an ice bath, followed by adding ethyl bromoacetate (1.16 g, 6.95 mmol), and the mixture was stirred for 2 hours. LC-MS detection showed that the reaction was completed. The reaction liquid was poured into water (30 mL), and was extracted by ethyl acetate (30 mL×3). Subsequently, the organic phases were combined, washed by saturated saline, dried by anhydrous sodium sulfate, concentrated under reduced pressure and residues were purified through a column chromatography (petroleum ether:ethyl acetate=1:2) to obtain a white solid product, i.e., ethyl 2-(4-(5-((5-cyano-4-(4 -fluorophenyl)thiazol-2-yl)(ethyl)amino)-6-ethylimidazo[2,1-b] thiazol-2-yl]piperidin-1-yl)acetate (2.31 g, 70%). LCMS [M+1]+: 567.2.

STEP 2): 2-(4-(5-((5-cyano-4-(4-fluorophenyl)thiazol-2-yl)(ethyl)amino)-6-ethylimidazo[2,1-b] thiazol-2-yl)piperidin-1-yl)acetic acid Lithium hydrate monohydrate (514 mg, 12.2 mmol) was added to a solution of ethyl 2-(4-(5-((5-cyano-4-(4-fluorophenyl)thiazol-2-yl)(ethyl)amino)-6-ethylimidazo[2,1-b] thiazol-2-yl]piperidin-1-yl)acetate (2.31 g, 4.08 mmol) in tetrahydrofuran (10 mL) and water (10 mL). The mixture was reacted at room temperature for 3 hours. LC-MS detection showed that the reaction was completed. After the reaction liquid was concentrated under reduced pressure, water (50 mL) was added to residues and 1N HCl was used for regulating pH at about 5. The liquid was filtered, and the filter cake was washed by water and dried to obtain a white solid product, i.e., 2-(4-(5-((5-cyano-4-(4-fluorophenyl)thiazol-2-yl)(ethyl)amino)-6-ethylimidazo[2,1-b] thiazol-2-yl] piperidin-1-yl)acetic acid (1.98 g, 90%). LCMS $[M+1]^+$: 539.2.

STEP 3): 2-(4-(5-((5-cyano-4-(4-fluorophenyl)thiazol-2-yl)(ethyl)amino)-6-ethylimidazo[2,1-b]thiazol-2-yl)piperidin-1-yl)-N-(2-hydroxyethyl)acetamide HATU (46 mg, 0.12 mmol), DIPEA (36 mg, 0.28 mmol), and ethanol amine (11 mg, 0.18 mmol) were successively added to a solution of 2-(4-(5-((5-cyano-4-(4-fluorophenyl) thiazol-2-yl)(ethyl)amino)-6-ethylimidazo[2,1-b] thiazol-2-yl]piperidin-1)acetic acid (50 mg, 0.093 mmol) in dichloromethane (3 mL). The mixture was stirred at room temperature for 2 hours, and then concentrated under reduced pressure. Subsequently, residues were purified by thick preparative plates (DCM:MeOH=15:1), to obtain a white solid product, i.e., 2-(4-(5-((5-cyano-4-(4-fluorophenyl)thiazol-2-yl)(ethyl)amino)-6-ethylimidazo[2,1-b]thiazol-2-yl]piperidin-1-yl)-N-(2-hydroxyethyl)acetamide (50 mg, 93%). $^1$H NMR (400 MHz, $CD_3OD$) δ: 8.12 (m, 2H), 7.52 (m, 1H), 7.25 (m, 2H), 4.17 (m, 1H), 4.01 (m, 1H), 3.73 (m, 2H), 3.61 (m, 2H), 3.35 (m, 2H), 3.24 (m, 2H), 3.11 (m, 2H), 3.03 (m, 1H), 2.88 (m, 1H), 2.60 (m, 2H), 2.37 (m, 1H), 2.03 (m, 2H), 1.88 (m, 2H), 1.30 (m, 6H). LCMS [M+1]+: 582.3.

Embodiment 4

Preparation of 2-(4-(5-((5-cyano-4-(4-fluorophenyl) thiazol-2-yl)(ethyl)amino)-6-ethylimidazo[2,1-b] thiazol-2-yl]piperidin-1-yl)-N-(2-hydroxyethyl)-N-methylacetamide

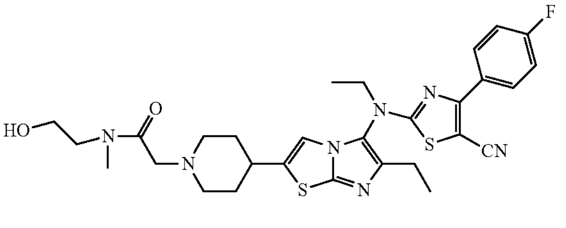 [SMILES: CCc1nc2sc(C3CCN(CC(=O)N(C)CCO)CC3)cn2c1N(CC)c1nc(-c2ccc(F)cc2)c(C#N)s1]

The title compound of Embodiment 4 was synthesized referring to the synthesis steps of Embodiment 3, apart from the fact that N-methyl-2-hydroxyethylamine was used to replace ethanol amine, and therefore a white solid product, i.e., 2-(4-(5-((5-cyano-4-(4-fluorophenyl)thiazol-2-yl)(ethyl)amino)-6-ethylimidazo[2,1-b]thiazol-2-yl]piperidin-1-yl)-N-(2-hydroxyethyl)-N-methylacetamide (43 mg, 78%) was obtained. $^1$H NMR (400 MHz, $CD_3OD$) δ: 8.13 (m, 2H), 7.54 (m, 1H), 7.25 (m, 2H), 4.17 (m, 1H), 4.01 (m, 1H), 3.71 (m, 2H), 3.52 (m, 4H), 3.35 (m, 2H), 3.22-3.12 (m, 3H), 2.96 (m, 2H), 2.94 (m, 1H), 2.87 (m, 1H), 2.61 (m, 2H), 2.47 (m, 1H), 2.09 (m, 2H), 1.87 (m, 2H), 1.30 (m, 6H). LCMS [M+1]+: 596.1.

Embodiment 5

Preparation of 2-(4-(5-((5-cyano-4-(4-fluorophenyl)thiazol-2-yl)(ethyl)amino)-6-ethylimidazo[2,1-b]thiazol-2-yl]piperidin-1-yl)-N-(3-hydroxycyclobutyl)acetamide

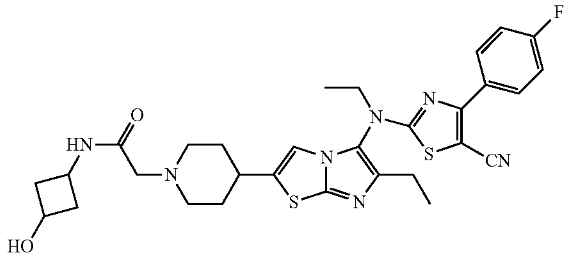 [SMILES: CCc1nc2sc(C3CCN(CC(=O)NC4CC(O)C4)CC3)cn2c1N(CC)c1nc(-c2ccc(F)cc2)c(C#N)s1]

The title compound of Embodiment 5 was synthesized referring to the synthesis steps of Embodiment 3, apart from the fact that 3-aminocyclobutanol was used to replace ethanol amine, and therefore a white solid product, i.e., 2-(4-(5-((5-cyano-4-(4-fluorophenyl)thiazol-2-yl)(ethyl)amino)-6-ethylimidazo[2,1-b]thiazol-2-yl]piperidin-1-yl)-N-(3-hydroxycyclobutyl) acetamide (41 mg, 73%) was obtained. $^1$H NMR (400 MHz, $CD_3OD$) δ: 8.13 (m, 2H), 7.53 (m, 1H), 7.25 (m, 2H), 4.17 (m, 1H), 4.00 (m, 2H), 3.87 (m, 1H), 3.73 (m, 1H), 3.24 (m, 2H), 3.12 (m, 2H), 3.03 (m, 2H), 2.88 (m, 1H), 2.68 (m, 1H), 2.61 (m, 2H), 2.39 (m, 2H), 2.28 (m, 2H), 2.06 (m, 2H), 1.86 (m, 3H), 1.30 (m, 6H). LCMS [M+1]+: 608.4.

Embodiment 6

Preparation of 2-((6-ethyl-2-(1-(2-(3-hydroxyazetidin-1-yl)-2-oxoethyl)piperidin-4-yl) imidazo[2,1-b]thiazol-5-yl)(2,2,2,-trifluoroethyl)amino)-4-(4-fluorophenyl)thiazole-5-carbonitrile

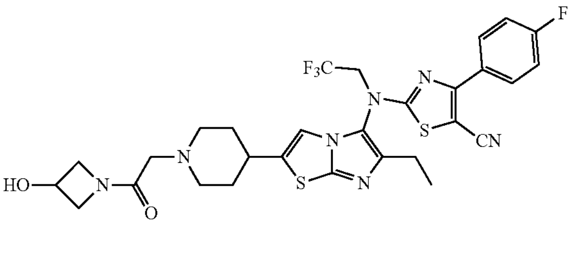 [SMILES: CCc1nc2sc(C3CCN(CC(=O)N4CC(O)C4)CC3)cn2c1N(CC(F)(F)F)c1nc(-c2ccc(F)cc2)c(C#N)s1]

The title compound of Embodiment 6 was synthesized referring to the synthesis steps of Embodiment 1, apart from the fact that 2,2,2,-trifluoroethyl trifluoromethanesulfonate was used to replace iodoethane, and therefore a white solid product, i.e., 2-((6-ethyl-2-(1-(2-(3-hydroxyazetidin-1-yl)-2-oxoethyl)piperidin-4-yl)imidazo[2,1-b]thiazol-5-yl)(2,2,2,-trifluoroethyl)amino)-4-(4-fluorophenyl)thiazole-5-carbonitrile (96 mg, 87%) was obtained. $^1$H NMR (400 MHz, $CD_3OD$) δ: 8.15 (m, 2H), 7.51 (m, 1H), 7.27 (m, 2H), 4.88 (m, 1H), 4.75 (m, 1H), 4.51 (m, 1H), 4.47 (m, 1H), 4.21 (m, 1H), 4.05 (m, 1H), 3.78 (m, 1H), 3.14 (m, 2H), 3.02 (m, 2H), 2.84 (m, 1H), 2.61 (m, 2H), 2.26 (m, 2H), 2.03 (m, 2H), 1.82 (m, 2H), 1.30 (m, 3H). LCMS $[M+1]^+$: 648.1.

Embodiment 7

Preparation of 2-((ethyl-$d_5$)(6-ethyl-2-(1-(2-(3-hydroxyazetidin-1-yl)-2-oxoethyl)piperidin-4-yl)imidazo[2,1-b]thiazol-5-yl)amino)-4-(4-fluorophenyl)thiazole-5-carbonitrile

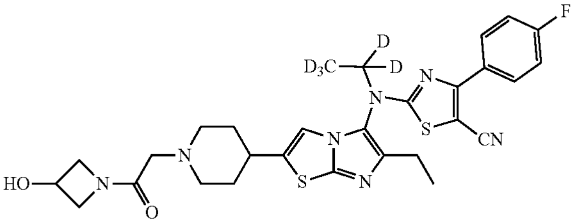 [SMILES: [2H]C([2H])([2H])C([2H])([2H])N(c1nc(-c2ccc(F)cc2)c(C#N)s1)c1c(CC)nc2sc(C3CCN(CC(=O)N4CC(O)C4)CC3)cn12]

The title compound of Embodiment 7 was synthesized referring to the synthesis steps of Embodiment 1, apart from the fact that iodoethane-$d_5$ was used to replace iodoethane, and therefore a white solid product, i.e., 2-((ethyl-$d_5$)(6-ethyl-2-(1-(2-(3-hydroxyazetidin-1-yl)-2-oxoethyl)piperidin-4-yl) imidazo[2,1-b]thiazol-5-yl)amino)-4-(4-fluorophenyl)thiazole-5-carbonitrile (76 mg, 76%). $^1$H NMR (400 MHz, $CD_3OD$) δ: 8.13 (m, 2H), 7.52 (m, 1H), 7.24 (m, 2H), 4.57 (m, 1H), 4.47 (m, 1H), 4.21 (m, 1H), 4.05 (m, 1H), 3.77 (m, 1H), 3.10 (m, 6H), 3.01 (m, 1H), 2.83 (m, 1H), 2.60 (m, 2H), 2.27 (m, 2H), 2.03 (m, 2H), 1.82 (m, 2H), 1.30 (m, 3H). LCMS $[M+1]^+$: 599.2

Embodiment 8

Preparation of 2-(4-(5-((5-cyano-4-(4-fluorophenyl)thiazol-2-yl)(ethyl)amino)-6-ethylimidazo[2,1-b]thiazol-2-yl)piperidin-1-yl)-N-(2-hydroxy-2-methylpropyl)acetamide

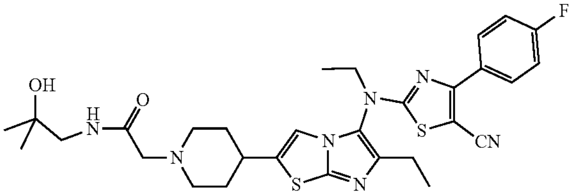 [SMILES: CCc1nc2sc(C3CCN(CC(=O)NCC(C)(C)O)CC3)cn2c1N(CC)c1nc(-c2ccc(F)cc2)c(C#N)s1]

The title compound of Embodiment 8 was synthesized referring to the synthesis steps of Embodiment 3, apart from the fact that 2-hydroxy-2-methylpropylamine was used to replace ethanolamine, and therefore a white solid product, i.e., 2-(4-(5-((5-cyano-4-(4-fluorophenyl)thiazol-2-yl)(ethyl)amino)-6-ethylimidazo[2,1-b]thiazol-2-yl)piperidin-1-yl)-N-(2-hydroxy-2-methylpropyl)acetamide (44 mg, 78%) was obtained. $^1$H NMR (400 MHz, $CD_3OD$) δ: 8.13 (m, 2H), 7.53 (m, 1H), 7.25 (m, 2H), 4.17 (m, 1H), 4.01 (m, 1H), 3.73 (m, 2H), 3.23 (m, 4H), 3.08 (m, 2H), 2.91 (m, 1H), 2.61 (m, 2H), 2.46 (m, 2H), 2.09 (m, 2H), 1.88 (m, 2H), 1.31 (m, 6H), 1.18 (m, 6H). LCMS [M+1]+: 610.3.

Embodiment 9

Preparation of 2-(4-(5-((5-cyano-4-(4-fluorophenyl)thiazol-2-yl)(ethyl)amino)-6-ethylimidazo[2,1-b]thiazol-2-yl)piperidin-1-yl)-N-(3-hydroxy-2,2-dimethylpropyl)acetamide

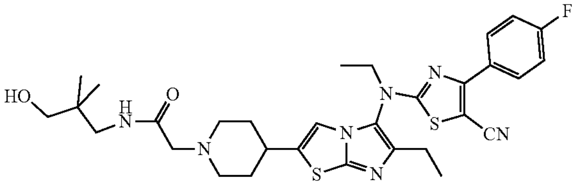 [SMILES: CCc1nc2sc(C3CCN(CC(=O)NCC(C)(C)CO)CC3)cn2c1N(CC)c1nc(-c2ccc(F)cc2)c(C#N)s1]

The title compound of Embodiment 9 was synthesized referring to the synthesis steps of Embodiment 3, apart from the fact that 3-hydroxy-2,2-dimethylpropylamine was used to replace ethanolamine, and therefore a white solid product, i.e., 2-(4-(5-((5-cyano-4-(4-fluorophenyl)thiazol-2-yl)(ethyl)amino)-6-ethylimidazo[2,1-b]thiazol-2-yl)piperidin-1-yl)-N-(3-hydroxy-2,2-dimethylpropyl)acetamide (44 mg, 76%) was obtained. $^1$H NMR (400 MHz, $CD_3OD$) δ: 8.13 (m, 2H), 7.53 (m, 1H), 7.25 (m, 2H), 4.18 (m, 1H), 4.00 (m, 1H), 3.73 (m, 2H), 3.27-3.21 (m, 4H), 3.16 (m, 3H), 3.05 (m, 2H), 2.89 (m, 1H), 2.61 (m, 2H), 2.43 (m, 1H), 2.07 (m, 2H), 1.88 (m, 2H), 1.31 (m, 6H), 0.88 (s, 6H). LCMS $[M+1]^+$: 624.2.

Embodiment 10

Preparation of 2-(4-(5-((5-cyano-4-(4-fluorophenyl)thiazol-2-yl)(ethyl)amino)-6-ethylimidazo[2,1-b]thiazol-2-yl)piperidin-1-yl)-N-(2-cyanoethyl)-N-methylacetamide

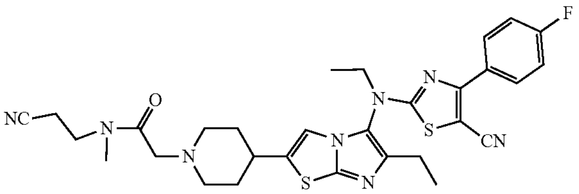 [SMILES: CCc1nc2sc(C3CCN(CC(=O)N(C)CCC#N)CC3)cn2c1N(CC)c1nc(-c2ccc(F)cc2)c(C#N)s1]

The title compound of Embodiment 10 was synthesized referring to the synthesis steps of Embodiment 3, apart from the fact that 3-methylaminopropionitrile was used to replace ethanolamine, and therefore a white solid product, i.e., 2-(4-(5-((5-cyano-4-(4-fluorophenyl)thiazol-2-yl)(ethyl)amino)-6-ethylimidazo[2,1-b]thiazol-2-yl)piperidin-1-yl)-N-(2-cyanoethyl)-N-methylacetamide (45 mg, 80%) was obtained. $^1$H NMR (400 MHz, $CD_3OD$) δ: 8.13 (m, 2H), 7.55 (m, 1H), 7.25 (m, 2H), 4.18 (m, 1H), 4.00 (m, 1H), 3.77-3.66 (m, 4H), 3.61 (m, 1H), 3.24 (m, 3H), 3.15 (m, 2H), 2.98 (m, 2H), 2.85 (m, 1H), 2.74 (m, 1H), 2.61 (m, 2H), 2.12 (m, 2H), 1.90 (m, 2H), 1.31 (m, 6H). LCMS $[M+1]^+$: 605.4

Embodiment 11

Preparation of 2-(4-(5-((5-cyano-4-(4-fluorophenyl)thiazol-2-yl)(ethyl)amino)-6-ethylimidazo[2,1-b]thiazol-2-yl)piperidin-1-yl)-N-(2,2-difluoroethyl)acetamide

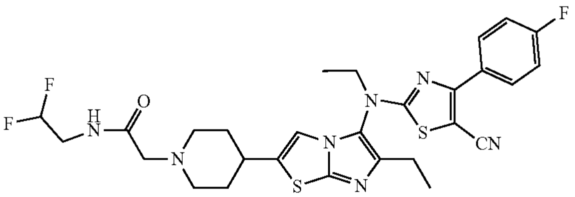 [SMILES: CCc1nc2sc(C3CCN(CC(=O)NCC(F)F)CC3)cn2c1N(CC)c1nc(-c2ccc(F)cc2)c(C#N)s1]

The title compound of Embodiment 11 was synthesized referring to the synthesis steps of Embodiment 3, apart from the fact that 2,2-difluoroethylamine was used to replace ethanolamine, and therefore a white solid product, i.e., 2-(4-(5-((5-cyano-4-(4-fluorophenyl)thiazol-2-yl)(ethyl)amino)-6-ethylimidazo[2,1-b] thiazol-2-yl)piperidin-1-yl)-N-(2,2-difluoroethyl)acetamide (38 mg, 68%) was obtained. $^1$H NMR (400 MHz, $CD_3OD$) δ: 8.13 (m, 2H), 7.54 (m, 1H), 7.26 (m, 2H), 5.93 (m, 1H), 4.19 (m, 1H), 4.03 (m, 1H), 3.63 (m, 2H), 3.14 (m, 2H), 3.02 (m, 2H), 2.91 (m, 1H), 2.83 (m, 1H), 2.63 (m, 1H), 2.36 (m, 2H), 2.03 (m, 2H), 1.89 (m, 2H), 1.32 (m, 6H). LCMS $[M+1]^+$: 602.2.

Embodiment 12

Preparation of 2-(4-(5-((5-cyano-4-(4-fluorophenyl)thiazol-2-yl)(ethyl)amino)-6-ethylimidazo[2,1-b]thiazol-2-yl)piperidin-1-yl)-N-(1-(hydroxymethyl)cyclopropyl)acetamide

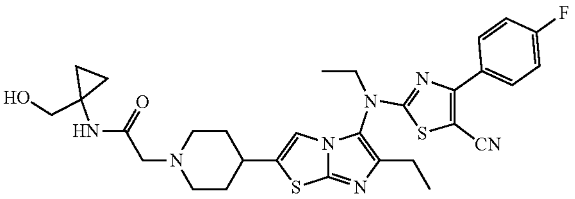 [SMILES: CCc1nc2sc(C3CCN(CC(=O)NC4(CO)CC4)CC3)cn2c1N(CC)c1nc(-c2ccc(F)cc2)c(C#N)s1]

The title compound of Embodiment 12 was synthesized referring to the synthesis steps of Embodiment 3, apart from the fact that 1-(aminocyclopropyl)methanol was used to replace ethanolamine, and therefore a white solid product, i.e., 2-(4-(5-((5-cyano-4-(4-fluorophenyl)thiazol-2-yl)(ethyl)amino)-6-ethylimidazo[2,1-b]thiazol-2-yl)piperidin-1-yl)-N-(1 -(hydroxymethyl)cyclopropyl) acetamide (47 mg, 83%) was obtained. $^1$H NMR (400 MHz, $CD_3OD$) δ: 8.14 (m, 2H), 7.52 (m, 1H), 7.25 (m, 2H), 4.17 (m, 1H), 4.01 (m, 1H), 3.73 (m, 1H), 3.59 (s, 2H), 3.22 (m, 1H), 3.06 (s, 2H), 2.97 (m, 2H), 2.85 (m, 1H), 2.60 (m, 2H), 2.32 (m, 2H), 2.04 (m, 2H), 1.85 (m, 2H), 1.31 (m, 6H), 0.80 (m, 4H). LCMS $[M+1]^+$: 608.3.

Embodiment 13

Preparation of 2-(4-(5-((5-cyano-4-(4-fluorophenyl) thiazol-2-yl)(ethyl)amino)-6-ethylimidazo[2,1-b] thiazol-2-yl)piperidin-1-yl)-N-(1-hydroxypropan-2-yl)acetamide

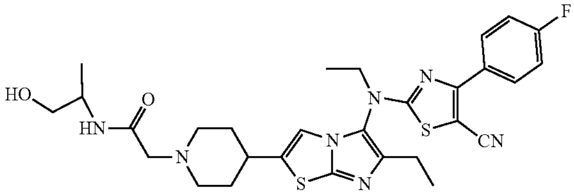 [SMILES: CCc1nc2sc(C3CCN(CC(=O)NC(C)CO)CC3)cn2c1N(CC)c1nc(-c2ccc(F)cc2)c(C#N)s1]

The title compound of Embodiment 13 was synthesized referring to the synthesis steps of Embodiment 3, apart from the fact that DL-aminopropanol was used to replace ethanolamine, and therefore a white solid product, i.e., 2-(4-(5-((5-cyano-4-(4-fluorophenyl)thiazol-2-yl)(ethyl)amino)-6-ethylimidazo[2,1-b]thiazol-2-yl)piperidin-1-yl)-N-(1-hydroxypropan-2-yl)acetamide (45 mg, 81%) was obtained. $^1$H NMR (400 MHz, $CD_3OD$: δ: 8.13 (m, 2H), 7.54 (m, 1H), 7.24 (m, 2H), 4.17 (m, 1H), 4.01 (m, 1H), 3.73 (m, 2H), 3.52 (m, 2H), 3.24 (m, 2H), 3.18 (m, 1H), 3.08 (m, 2H), 2.91 (m, 1H), 2.61 (m, 2H), 2.45 (m, 1H), 2.08 (m, 2H), 1.88 (m, 2H), 1.30 (m, 6H), 1.15 (m, 3H). LCMS $[M+1]^+$: 565.2.

Embodiment 14

Preparation of 2-(4-(5-((5-cyano-4-(4-fluorophenyl) thiazol-2-yl)(ethyl)amino)-6-ethylimidazo[2,1-b] thiazol-2-yl)piperidin-1-yl)-N-(1-hydroxy-2-methyl-propan-2-yl)acetamide

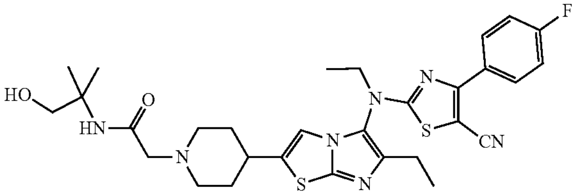 [SMILES: CCc1nc2sc(C3CCN(CC(=O)NC(C)(C)CO)CC3)cn2c1N(CC)c1nc(-c2ccc(F)cc2)c(C#N)s1]

The title compound of Embodiment 14 was synthesized referring to the synthesis steps of Embodiment 3, apart from the fact that 2-amino-2-methyl-1-propanol was used to replace ethanolamine, and therefore a white solid product, i.e., 2-(4-(5-((5-cyano-4-(4-fluorophenyl)thiazol-2-yl)(ethyl)amino)-6-ethylimidazo[2,1-b]thiazol-2-yl)piperidin-1-yl)-N-(1-hydroxy-2-methylpropan-2-yl)acetamide (41 mg, 72%) was obtained. $^1$H NMR (400 MHz, $CD_3OD$) δ: 8.13 (m, 2H), 7.53 (m, 1H), 7.24 (m, 2H), 4.19 (m, 1H), 4.01 (m, 1H), 3.73 (m, 1H), 3.54 (m, 2H), 3.22 (m, 1H), 3.04 (m, 4H), 2.88 (m, 1H), 2.61 (m, 2H), 2.40 (m, 2H), 2.08 (m, 2H), 1.84 (m, 2H), 1.30 (m, 12H). LCMS $[M+1]^+$: 610.2.

Embodiment 15

Preparation of 2-(4-(5-((5-cyano-4-(4-fluorophenyl) thiazol-2-yl)(ethyl)amino)-6-ethylimidazo[2,1-b] thiazol-2-yl)piperidin-1-yl)-N-((1-hydroxycyclopropyl)methyl)acetamide

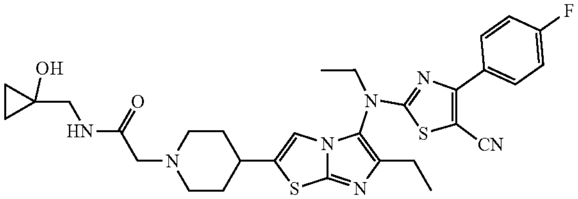 [SMILES: CCc1nc2sc(C3CCN(CC(=O)NCC4(O)CC4)CC3)cn2c1N(CC)c1nc(-c2ccc(F)cc2)c(C#N)s1]

The title compound of Embodiment 15 was synthesized referring to the synthesis steps of Embodiment 3, apart from the fact that 1-(aminomethyl)cyclopropanol was used to replace ethanolamine, and therefore a white solid product, i.e., 2-(4-(5-((5-cyano-4-(4-fluorophenyl)thiazol-2-yl)(ethyl)amino)-6-ethylimidazo[2,1-b] thiazol-2-yl)piperidin-1-yl)-N-(1-hydroxycyclopropyl)methyl)acetamide (38 mg, 67%) was obtained. $^1$H NMR (400 MHz, $CD_3OD$) δ: 8.13 (m, 2H), 7.54 (m, 1H), 7.25 (m, 2H), 4.17 (m, 1H), 4.01 (m, 1H), 3.73 (m, 2H), 3.37 (s, 2H), 3.24-3.19 (m, 4H), 3.10 ((m, 2H), 2.91 (m, 1H), 2.61 (m, 2H), 2.45 (m, 2H), 2.09 (m, 2H), 1.89 (m, 2H), 1.31 (m, 6H), 0.70 (m, 2H), 0.60 (m, 2H). LCMS $[M+1]^+$: 608.2.

Embodiment 16

Preparation of 2-(4-(5-((5-cyano-4-(4-fluorophenyl) thiazol-2-yl)(ethyl)amino)-6-ethylimidazo[2,1-b] thiazol-2-yl)piperidin-1-yl)-N-((1-hydroxycyclobutyl)methyl) acetamide

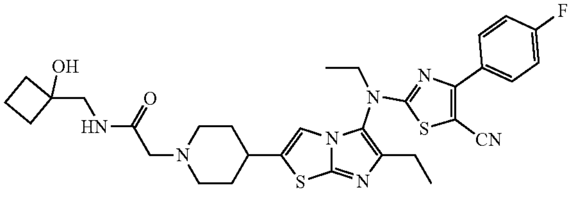 [SMILES: CCc1nc2sc(C3CCN(CC(=O)NCC4(O)CCC4)CC3)cn2c1N(CC)c1nc(-c2ccc(F)cc2)c(C#N)s1]

The title compound of Embodiment 16 was synthesized referring to the synthesis steps of Embodiment 3 apart from the fact that 1-(aminomethyl)cyclobutanol was used to replace ethanolamine, and therefore a white solid product, i.e., 2-(4-(5-((5-cyano-4-(4-fluorophenyl)thiazol-2-yl)(ethyl)amino)-6-ethylimidazo[2,1-b]thiazol-2-yl)piperidin-1-yl)-N-((1-hydroxycyclobutyl)methyl) acetamide (41 mg, 71%) was obtained. $^1$H NMR (400 MHz, $CD_3OD$) δ: 8.13 (m, 2H), 7.51 (m, 1H), 7.25 (m, 2H), 4.17 (m, 1H), 4.01 (m, 1H), 3.39 (s, 2H), 3.09 (m, 2H), 2.97 (m, 2H), 2.87-2.81 (m, 2H), 2.61 (m, 2H), 2.32 (m, 2H), 2.03 (m, 6H), 1.84 (m, 2H), 1.75 (m, 2H), 1.61 (m, 1H), 1.31 (m, 6H). LCMS $[M+1]^+$: 622.2.

Embodiment 17

Preparation of 2-(4-(5-((5-cyano-4-(4-fluorophenyl) thiazol-2-yl)(ethyl)amino)-6-ethylimidazo[2,1-b] thiazol-2-yl)piperidin-1-yl)-N-(3,3-difluorocyclobutyl)acetamide

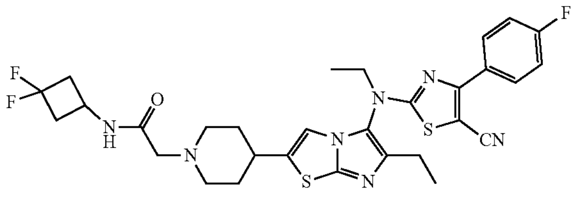 [SMILES: CCc1nc2sc(C3CCN(CC(=O)NC4CC(F)(F)C4)CC3)cn2c1N(CC)c1nc(-c2ccc(F)cc2)c(C#N)s1]

The title compound of Embodiment 17 was synthesized referring to the synthesis steps of Embodiment 3, apart from the fact that 3,3-difluorocyclobutylamine was used to replace ethanolamine, and therefore a white solid product, i.e., 2-(4-(5-((5-cyano-4-(4-fluorophenyl)thiazol-2-yl)(ethyl)amino)-6-ethylimidazo[2,1-b]thiazol-2-yl)piperidin-1-yl)-N-(3,3-difluoroclobutyl)acetamide (43 mg, 74%) was obtained. $^1$H NMR (400 MHz $CD_3OD$) δ: 8.13 (m, 2H), 7.51 (m, 1H), 7.25 (m, 2H), 4.17 (m, 2H), 4.01 (m, 1H), 3.03 (s, 2H), 2.96-2.81 (m, 5H), 2.67-2.56 (m, 4H), 2.87-2.81 (m, 2H), 2.28 (m, 2H), 2.02 (m, 2H), 1.86 (m, 2H), 1.31 (m, 6H). LCMS $[M+1]^+$: 627.1.

Embodiment 18

Preparation of 2-(4-(5-((5-cyano-4-(4-fluorophenyl) thiazol-2-yl)(ethyl)amino)-6-ethylimidazo[2,1-b] thiazol-2-yl)piperidin-1-yl)-N-(cyclopropylmethyl) acetamide

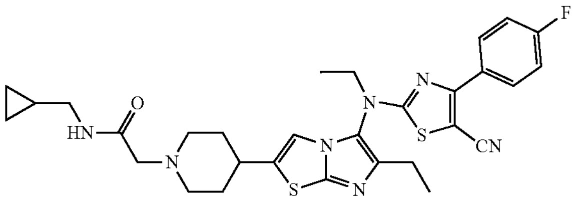 [SMILES: CCc1nc2sc(C3CCN(CC(=O)NCC4CC4)CC3)cn2c1N(CC)c1nc(-c2ccc(F)cc2)c(C#N)s1]

The title compound of Embodiment 18 was synthesized referring to the synthesis steps of Embodiment 3, apart from the fact that cyclopropylmethanamine was used to replace ethanolamine, and therefore a white solid product, i.e., 2-(4-(5-((5-cyano-4-(4-fluorophenyl)thiazol-2-yl)(ethyl)amino)-6-ethylimidazo[2,1-b]thiazol-2-yl)piperidin-1-yl)-N-(cyclopropylmethyl)acetamide (38 mg, 69%) was obtained. $^1$H NMR (400 MHz, $CD_3OD$) δ: 8.13 (m, 2H), 7.52 (m, 1H), 7.25 (m, 2H), 4.17 (m, 1H), 4.01 (m, 1H), 3.10 (m, 2H), 3.04 (m, 2H), 2.99 (m, 4H), 2.86 (m, 1H), 2.61 (m, 2H), 2.32 (m, 2H), 2.04 (m, 2H), 1.86 (m, 2H), 1.31 (m, 6H), 0.49 (m, 2H), 0.22 (m, 2H). LCMS $[M+1]^+$: 592.1.

Embodiment 19

Preparation of 2-(4-(5-((5-cyano-4-(4-fluorophenyl) thiazol-2-yl)(ethyl)amino)-6-ethylimidazo[2,1-b] thiazol-2-yl)piperidin-1-yl)-N-(cyclobutylmethyl) acetamide

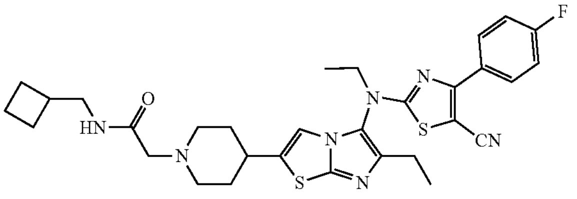 [SMILES: CCc1nc2sc(C3CCN(CC(=O)NCC4CCC4)CC3)cn2c1N(CC)c1nc(-c2ccc(F)cc2)c(C#N)s1]

The title compound of Embodiment 19 was synthesized referring to the synthesis steps of Embodiment 3 apart from the fact that cyclobutylmethanamine a was used to replace ethanolamine, and therefore a white solid product, i.e., 2-(4-(5-((5-cyano-4-(4-fluorophenyl)thiazol-2-yl)(ethyl)amino)-6-ethylimidazo[2,1-b]thiazol-2-yl)piperidin-1-yl)-N-(cyclobutylmethyl)acetamide (40 mg, 71%) was obtained. $^1$H NMR (400 MHz, $CD_3OD$) δ: 8.13 (m, 2H), 7.51 (m, 1H), 7.24 (m, 2H), 4.17 (m, 1H), 4.01 (m, 1H), 3.24 (m, 2H), 3.22 (m, 1H), 3.02 (m, 2H), 2.98 (m, 6H), 2.94 (m, 1H), 2.81 (m, 1H), 2.63-2.50 (m, 2H), 2.29 (m, 2H), 2.03 (m, 2H), 1.87 (m, 2H), 1.74 (m, 2H), 1.31 (m, 2H). LCMS $[M+1]^+$: 606.2.

Embodiment 20

Preparation of 2-(4-(5-((5-cyano-4-(4-fluorophenyl) thiazol-2-yl)(ethyl)amino)-6-ethylimidazo[2,1-b] thiazol-2-yl)piperidin-1-yl)-N-tert-pentylacetamide

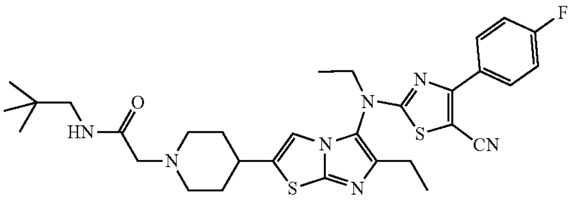 [SMILES: CCc1nc2sc(C3CCN(CC(=O)NCC(C)(C)C)CC3)cn2c1N(CC)c1nc(-c2ccc(F)cc2)c(C#N)s1]

The title compound of Embodiment 20 was synthesized referring to the synthesis steps of Embodiment 3 apart from the fact that tert-pentylamine was used to replace ethanolamine, and therefore a white solid product, i.e., 2-(4-(5-((5-cyano-4-(4-fluorophenyl)thiazol-2-yl)(ethyl)amino)-6-ethylimidazo[2,1-b]thiazol-2-yl)piperidin-1-yl)-N-tert-pentylacetamide (37 mg, 66%) was obtained. $^1$H NMR (400 MHz, $CD_3OD$) δ: 8.13 (m, 2H), 7.53 (m, 1H), 7.25 (m, 2H), 4.19 (m, 1H), 4.01 (m, 1H), 3.06 (m, 3H), 2.99 (m, 2H), 2.91-2.81 (m, 3H), 2.61 (m, 2H), 2.33 (m, 2H), 2.06-1.81 (m, 2H), 1.31 (m, 6H), 0.92 (s, 9H). LCMS $[M+1]^+$: 608.2.

Embodiment 21

Preparation of 2-(4-(5-((5-cyano-4-(4-fluorophenyl) thiazol-2-yl)(ethyl)amino)-6-ethylimidazo[2,1-b] thiazol-2-yl)piperidin-1-yl)-N-(3-oxacyclobutyl) acetamide

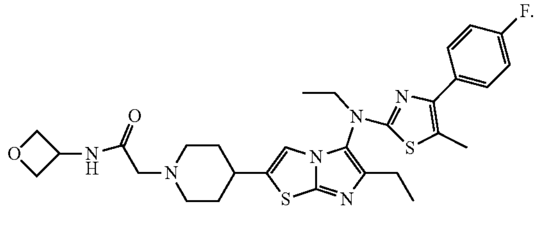 [SMILES: CCc1nc2sc(C3CCN(CC(=O)NC4COC4)CC3)cn2c1N(CC)c1nc(-c2ccc(F)cc2)c(C)s1]

The title compound of Embodiment 21 was synthesized referring to the synthesis steps of Embodiment 3, apart from the fact that 3-oxacyclobutylamine was used to replace ethanolamine, and therefore a white solid product, i.e., 2-(4-(5-((5-cyano-4-(4-fluorophenyl)thiazol-2-yl)(ethyl) amino)-6-ethylimidazo[2,1-b]thiazol-2-yl)piperidin-1-yl)-N-(3-oxacyclobutyl)acetamide (39 mg, 71%) was obtained. $^1$H NMR (400 MHz, $CD_3OD$) δ: 8.13 (m, 2H), 7.52 (m, 1H), 7.25 (m, 2H), 4.96 (m, 1H), 4.87 (m, 1H), 4.60 (m, 2H), 4.17 (m, 1H), 4.02 (m, 2H), 3.06 (s, 2H), 2.98 (m, 2H), 2.82 (m, 2H), 2.61 (m, 2H), 2.29 (m, 2H), 2.03 (m, 2H), 1.88 (m, 2H), 1.31 (m, 6H). LCMS [M+1]: 594.1.

Embodiment 22

Preparation of 2-(ethyl(6-ethyl-2-(1-(2-morpholino-2-oxoethyl)piperidin-4-yl) imidazo[2,1-b]thiazol-5-yl)amino)-4-(4-fluorophenyl)thiazole-5-carbonitrile

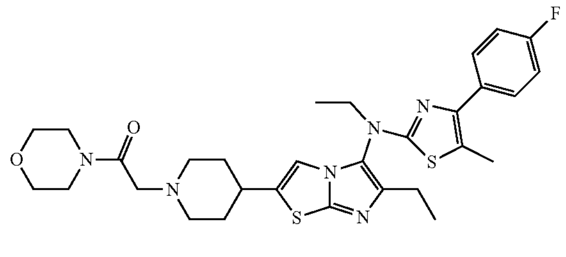 [SMILES: CCc1nc2sc(C3CCN(CC(=O)N4CCOCC4)CC3)cn2c1N(CC)c1nc(-c2ccc(F)cc2)c(C)s1]

The title compound of Embodiment 22 was synthesized referring to the synthesis steps of Embodiment 3, apart from the fact that morpholine was used to replace ethanolamine, and therefore a white solid product, i.e., 2-(ethyl(6-ethyl-2-(1-(2-morpholino-2-oxoethyl)piperidin-4-yl) imidazo[2,1-b]thiazol-5-yl)amino)-4-(4-fluorophenyl)thiazole-5-carbonitrile (41 mg, 73%) was obtained. $^1$H NMR (400 MHz, $CD_3OD$) δ: 8.13 (m, 2H), 7.52 (m, 1H), 7.25 (m, 2H), 4.17 (m, 1H), 4.00 (m, 1H), 3.65 (m, 5H), 3.58 (m, 2H), 3.03-3.96 (m, 5H), 2.87 (m, 1H), 2.61 (m, 2H), 2.25 (m, 2H), 2.04 (m, 2H), 1.78 (m, 2H), 1.30 (m, 6H). LCMS $[M+1]^+$: 608.1.

Embodiment 23

Preparation of 2-(4-(5-((5-cyano-4-(4-fluorophenyl) thiazol-2-yl)(ethyl)amino)-6-ethylimidazo[2,1-b] thiazol-2-yl)piperidin-1-yl)-N-(tetrahydro-2H-pyran-4-yl)acetamide

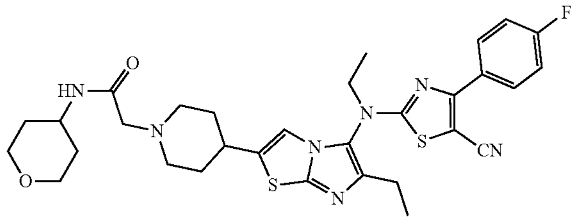 [SMILES: CCc1nc2sc(C3CCN(CC(=O)NC4CCOCC4)CC3)cn2c1N(CC)c1nc(-c2ccc(F)cc2)c(C#N)s1]

The title compound of Embodiment 23 was synthesized referring to the synthesis steps of Embodiment 3, apart from the fact that 4-aminotetrahydropyrane was used to replace ethanolamine, and therefore a white solid product, i.e., 2-(4-(5-((5-cyano-4-(4-fluorophenyl)thiazol-2-yl)(ethyl) amino)-6-ethylimidazo[2,1-b]thiazol-2-yl)piperidin-1-yl)-N-(tetrahydro-2H-pyran-4-yl)acetamide (45 mg, 78%) was obtained. $^1$H NMR (500 MHz, $CDCl_3$) δ: 8.15 (m, 2H), 7.19 (m, 2H), 7.02 (m, 1H), 6.96 (m, 1H), 4.12 (m, 1H), 4.05-3.96 (m, 4H), 3.51 (m, 2H), 3.04 (m, 2H), 2.96 (m, 2H), 2.76 (m, 1H), 2.62 (m, 2H), 2.31 (m, 2H), 2.06 (m, 2H), 1.90 (m, 2H), 1.77 (m, 2H), 1.52 (m, 2H), 1.34 (m, 6H). LCMS $[M+1]^+$: 622.3.

Embodiment 24

Preparation of 2-(cyclopropyl(6-ethyl-2-(1-(2-(3-hydroxyazetidin-1-yl)-2-oxoethyl)piperidin-4-yl) imidazo[2,1-b]thiazol-5-yl)amino)-4-(4-fluorophenyl)thiazole-5-carbonitrile

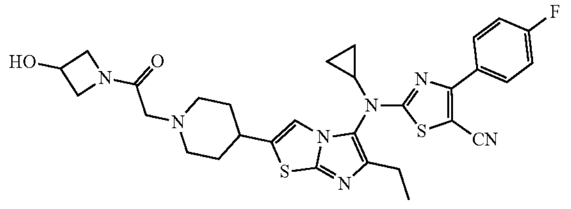 [SMILES: CCc1nc2sc(C3CCN(CC(=O)N4CC(O)C4)CC3)cn2c1N(c1nc(-c2ccc(F)cc2)c(C#N)s1)C1CC1]

STEP 1) tert-butyl 4-(5-((5-cyano-4-(4-fluorophenyl)thiazol-2-yl)amino)-6-ethylimidazo[2,1-b]thiazol-2-yl)piperidine-1-carboxylate Sodium hydrogen (306 mg, 7.65 mmol) was added to a solution of tert-butyl 4-(5-acetamido-6-ethylimidazo[2,1-b] thiazol-2-yl)piperidine-1-carboxylate (1 g, 2.55 mmol) in tetrahydrofuran (15 mL) in batches at 0° C. After the mixture was stirred for 10 min, a solution of 2-chloro-4-(4-fluorophenyl)thiazole-5-carbonitrile (596 mg, 2.50 mmol) in tetrahydrofuran (5 mL) was dripped to the mixture, and the temperature of the mixture was increased to room temperature for reaction. LCMS detection showed that the reaction was completed. Subsequently, the reaction liquid was poured into water, and the liquid was extracted by ethyl acetate (15 mL×3). Then, the organic phases were combined, washed by saturated saline, dried by anhyrous sodium sulfate, and concentrated under reduced pressure. The residues were purified by a column chromatography (petroleum ether:ethyl acetate=4:1 to 1.5:1) to obtain a yellow foam solid product, i.e., tert-butyl 4-(5-((5-cyano-4-(4-fluorophenyl)thiazol-2-yl)amino)-6-ethylimidazo[2,1-b]thiazol-2-yl) piperidine-1-carboxylate (980 mg, 70%). LCMS $[M+1]^+$: 553.3

STEP 2) tert-butyl 4-(5-((5-cyano-4-(4-fluorophenyl)thiazol-2-yl)(cyclopropyl)amino)-6-ethylimidazo[2,1-b]thiazol-2-yl)piperidine-1-carboxylate Cyclopropyl boracic acid (156 mg, 1.8 mmol), copper acetate (108 mg, 0.60 mmol), 2,2'-dipyridyl (96 mg, 0.60 mmol), and sodium carbonate (192 mg, 1.8 mmol) were added to a solution of tert-butyl 4-(5-((5-cyano-4-(4-fluorophenyl)thiazol-2-yl)amino)-6-ethylimidazo[2,1-b]thiazol-2-yl)piperidine-1-carboxylate (330 mg, 0.60 mmol) in 1,2-dichloroethane (10 mL), and the mixture was reacted overnight at 75° C. under an oxygen condition (balloon). The reaction liquid was filtered by siliceous earth and concentrated under reduced pressure. The residues were purified by a column chromatography (petroleum ether:ethyl acetate=5:1 to 3:1) to obtain a light yellow foam solid product, i.e., tert-butyl 4-(5-((5-cyano-4-(4-fluorophenyl) thiazol-2-yl) (cyclopropyl)amino)-6-ethylimidazo[2,1-b]thiazol-2-yl)piperidine-1-carboxylate (287 mg, 71%). LCMS $[M+1]^+$: 593.3.

STEP 3) 2-(cyclopropyl(6-ethyl-2-(piperidin-4-yl) imidazo[2,1-b]thiazol-5-yl)amino)-4-(4-fluorophenyl)thiazole-5-carbonitrile Trifluoroacetic acid (0.5 mL) was added to a solution of tert-butyl 4-(5-((5-cyano-4-(4-fluorophenyl)thiazol-2-yl) (cyclopropyl)amino)-6-ethylimidazo[2,1-b]thiazol-2-yl)piperidine-1-carboxylate (287 mg, 0.48 mmol) in dichloromethane (3 mL). The mixture was reacted for 2 hours at room temperature, and the reaction liquid was concentrated under reduced pressure. Water (15 mL) and dichloromethane (15 mL) were added to residues, and sodium bicarbonate was used for regulating pH to about 8. The liquid was extracted by dichloromethane (15 mL×2). Subsequently, the organic phases were combined, dried by anhydrous sodium sulfate, and concentrated under reduced pressure to obtain a light yellow foam solid product, i.e., 2-(cyclopropyl(6-ethyl-2-(piperidin-4-yl)imidazo[2,1-b]thiazol-5-yl)amino)-4-(4-fluorophenyl)thiazole-5-carbonitrile (230 mg, 96%). LCMS $[M+1]^+$: 493.3.

STEP 4) 2-(cyclopropyl-(6-ethyl-2-(1-(2-(3-hydroxyazetidin-1-yl)-2-oxoethyl)piperidin-4-yl)imidazo[2,1-b]thiazol-5-yl)amino)-4-(4-fluorophenyl) thiazole-5-carbonitrile 2-chloro-1-(3-hydroxyazetidin-1-yl)aceton (15 mg, 0.1 mmol), potassium carbonate (27 mg, 0.2 mmol), and potassium iodide (8.3 mg, 0.050 mmol) were added to a solution of 2-(cyclopropyl(6-ethyl-2-(piperidin-4-yl)imidazo[2,1-b] thiazol-5-yl)amino)-4-(4 -fluorophenyl)thiazole-5-carbonitrile (50 mg, 0.1 mmol) in acetonitrile (3 mL), and the mixture was reacted for 2 hours at 70° C. Subsequently, the reaction liquid was concentrated under reduced pressure, and residues were purified by thick preparative plates (dichloromethane:isopropanol=12:1) to obtain a white solid product, i.e., 2-(cyclopropyl-(6-ethyl-2-(1-(2-(3-hydroxyazetidin-1-yl)-2-oxoethyl)piperidin-4-yl)imidazo[2,1-b]thiazol-5-yl)amino)-4-(4-fluorophenyl)thiazole-5-carbonitrile (40 mg, 66%). $^1H$ NMR (500 MHz, $CDCl_3$) δ: 8.09 (m, 2H), 7.15 (m, 2H), 6.89 (m, 1H), 4.93 (m, 1H), 4.68 (m, 1H), 4.45 (m, 1H), 4.30 (m, 1H), 4.10 (m, 1H), 3.99 (m, 1H), 3.07-2.95 (m, 3H), 2.70 (m, 1H), 2.54 (m, 2H), 2.21 (m, 2H), 2.01 (m, 2H), 1.81 (m, 2H), 1.27 (m, 3H), 0.95 (m, 2H), 0.73 (m, 2H). LCMS $[M+1]^+$: 606.3.

Embodiment 25

Preparation of 2-((6-ethyl-2-(1-(2-(3-hydroxyazetidin-1-yl)-2-oxoethyl)piperidin-4-yl)imidazo[2,1-b] thiazol-5-yl)(isopropyl)amino)-4-(4-fluorophenyl) thiazole-5-carbonitrile

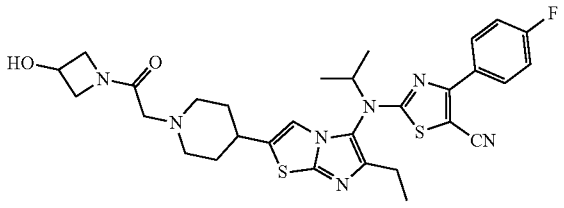 [SMILES: CCc1nc2sc(C3CCN(CC(=O)N4CC(O)C4)CC3)cn2c1N(c1nc(-c2ccc(F)cc2)c(C#N)s1)C(C)C]

STEP 1) Preparation of tert-butyl 4-(5-((5-cyano-4-(4-fluorophenyl)thiazol-2-yl)(isopropyl)amino)-6-ethylimidazo[2,1-b]thiazol-2-yl)piperidine-1-carboxylate Sodium hydrogen (72 mg, 1.8 mmol) was added to a solution of tert-butyl 4-(5-((5-cyano-4-(4-fluorophenyl)thiazol-2-yl)amino)-6-ethylimidazo[2,1-b]thiazol-2-yl)piperidine-1-carboxylate (330 mg, 0.60 mmol) in DMF (9 mL). After the mixture was stirred for 5 min at room temperature, 2-bromopropane (282 μL, 3.0 mmol) was added to the mixture, and the mixture was reacted at 85° C. After TLC detection showed that the reaction was completed, the reaction liquid was cooled to 0° C., and water was dripped to the liquid for performing a quenched reaction, Subsequently, water (15 mL) was added to the liquid, and the liquid was extracted by ethyl acetate (15 mL×3). Then, the organic phases were combined, washed by saturated saline, dried by anhyrous sodium sulfate, and concentrated by reduced pressure. The residues were purified through a column chromatography (petroleum ether:ethyl acetate=4:1 to 3:1) to obtain a light yellow foam solid product, i.e., tert-butyl 4-(5-((5-cyano-4-(4-fluorophenyl)thiazol-2-yl) (isopropyl)amino)-6-ethylimidazo[2,1-b]thiazol-2-yl)piperidine-1-carboxylate (365 mg, 89%). LCMS $[M+1]^+$: 595.3.

STEP 2) 2-((6-ethyl-2-(piperidin-4-yl)imidazo[2,1-b]thiazol-5-yl)(isopropyl)amino)-4-(4-fluorophenyl) thiazole-5-carbonitrile Trifluoroacetic acid (0.45 mL) was added to a solution of tert-butyl 4-(5-((5-cyano-4-(4-fluorophenyl)thiazol-2-yl) (isopropyl)amino)-6-ethylimidazo[2,1-b]thiazol-2-yl)piperidin-1-carboxylate (365 mg, 0.61 mmol) in dichloromethane (4 mL). The mixture was reacted for 2 hours at room temperature, and concentrated under reduced pressure. Water (15 mL) and dichloromethane (15 mL) were added to the reaction liquid, and sodium bicarbonate was used for regulating pH to about 8. Then, the liquid was extracted by dichloromethane (15 mL×2). The organic phases were combined, dried by anhydrous sodium sulfate, and concentrated under reduced pressure to obtain a light yellow foam solid product, i.e., 2-((6-ethyl-2-(piperidin-4-yl)imidazo[2,1-b]thiazol-5-yl)(isopropyl)amino)-4-(4-fluorophenyl)thiazole-5-carbonitrile (290 mg, %%). LCMS $[M+1]^+$: 495.3.

STEP 3) 2-((6-ethyl-2-(1-(2-(3-hydroxyazetidin-1-yl)-2-oxoethyl)piperidin-4-yl) imidazo[2,1-b]thiazol-5-yl)(isopropyl)amino)-4-(4-fluorophenyl)thiazole-5-carbonitrile 2-chloro-1-(3-hydroxyazetidin-1-yl)aceton (15 mg, 0.1 mmol), sodium bicarbonate (21 mg, 0.25 mmol), and potassium iodide (8.3 mg, 0.050 mmol) were added to a solution of 24(6-ethyl-2-(piperidin-4-yl)imidazo[2,1-b]thiazol-5-yl)(isopropyl)amino)-4-(4-fluorophenyl)thiazole-5-carbonitrile (50 mg, 0.1 mmol) in acetonitrile (3 mL), and the mixture was reacted for 3 hours at 70° C. The reaction liquid was filtered, and concentrated under reduced pressure. The residues were purified by thick preparative plates (dichloromethane:isopropanol=12:1) to obtain a white solid product, i.e., 2-((6-ethyl-2-(1-(2-(3-hydroxyazetidin-1-yl)-2-oxoethyl)piperidin-4-yl)imidazo[2,1-b]thiazol-5-yl)(isopropyl)amino)-4-(4-fluorophenyl)thiazole-5-carbonitrile (35 mg, 57%). $^1H$ NMR (500 MHz, $CDCl_3$) δ: 8.15 (m, 2H), 7.18 (m, 2H), 6.94 (m, 1H), 5.11 (m, 1H), 4.71 (m, 1H), 4.47 (m, 1H), 4.30 (m, 1H), 4.12 (m, 1H), 3.92 (m, 1H), 3.11-3.05 (m, 4H), 2.73 (m, 1H), 2.60 (m, 3H), 2.30 (m, 2H), 2.03 (m, 2H), 1.86 (m, 2H), 1.33 (m, 6H), 1.27 (m, 3H). LCMS $[M+1]^+$: 608.3.

Embodiment 26

Preparation of 2-(4-(5-((5-cyano-4-(4-fluorophenyl)thiazol-2-yl)(isopropyl)amino)-6-ethylimidazo[2,1-b]thiazol-2-yl)piperidin-1-yl)-N-(tetrahydro-2H-pyran-4-yl)acetamide

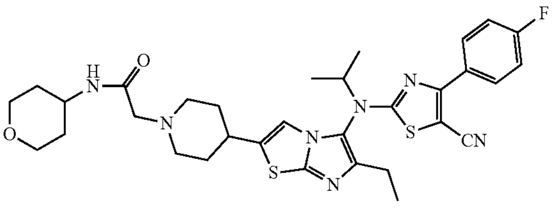 [SMILES: CCc1nc2sc(C3CCN(CC(=O)NC4CCOCC4)CC3)cn2c1N(c1nc(-c2ccc(F)cc2)c(C#N)s1)C(C)C]

The title compound of Embodiment 26 was synthesized referring to the synthesis steps of Embodiment 25, apart from the fact that 2-chloro-N-(tetrahydro-2H-pyran-4-yl)acetamide was used to replace 2-chloro-1-(3-hydroxyazetidin-1-yl)aceton, and therefore a white solid product, i.e., 2-(4-(5-((5-cyano-4-(4-fluorophenyl)thiazol-2-yl)(isopropyl)amino)-6-ethylimidazo[2,1-b]thiazol-2-yl)piperidin-1-yl)-N-(tetrahydro-2H-pyran-4-yl)acetamide (50 mg, 72%). $^1H$-NMR (400 MHz, $CDCl_3$) δ: 8.15 (m, 2H), 7.19 (m, 2H), 7.05-6.98 (m, 1H), 6.96 (s, 1H), 5.12 (m, 1H), 4.08-4.00 (m, 1H), 4.00-3.94 (m, 2H), 3.54-3.48 (m, 2H), 3.03 (s, 2H), 2.98-2.92 (m, 2H), 2.76 (m, 1H), 2.63-2.59 (m, 2H), 2.30 (m, 2H), 2.07-2.04 (m, 2H), 1.92-1.88 (m, 2H), 1.82-1.72 (m, 2H), 1.56-1.48 (m, 2H), 1.37-1.32 (m, 6H), 1.29-1.26 (m, 3H). LCMS [M+1]+: 636.3.

Embodiment 27

Preparation of 2-(4-(5-((5-cyano-4-(4-fluorophenyl)thiazol-2-yl)(isopropyl)amino)-6-ethylimidazo[2,1-b]thiazol-2-yl)piperidin-1-yl)-N-(oxacyclobut-3-yl)acetamide

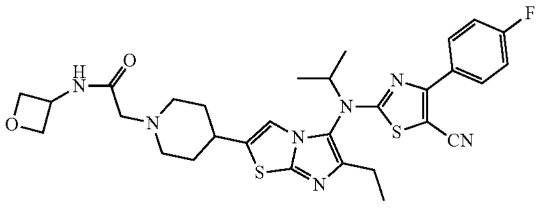 [SMILES: CCc1nc2sc(C3CCN(CC(=O)NC4COC4)CC3)cn2c1N(c1nc(-c2ccc(F)cc2)c(C#N)s1)C(C)C]

The title compound of Embodiment 27 was synthesized referring to the synthesis steps of Embodiment 25, apart from the fact that 2-chloro-N-(oxacyclobut-3-yl)acetamide was used to replace 2-chloro-1-(3-hydroxyazetidin-1-yl)aceton, and therefore a white solid product, i.e., 2-(4-(5-((5-cyano-4-(4-fluorophenyl)thiazol-2-yl)(isopropyl)amino)-6-ethylimidazo[2,1-b]thiazol-2-yl)piperidin-1-yl)-N-(oxacyclobut-3-yl)acetamide (48 mg, 72%). $^1H$-NMR (400 MHz, $CDCl_3$) δ: 8.15 (m, 2H), 7.71-7.60 (m, 1H), 7.19 (m, 2H), 6.98 (s, 1H), 5.16-5.07 (m, 2H), 4.98 (m, 2H), 4.54 (m, 2H), 3.06 (s, 2H), 3.00-2.95 (m, 2H), 2.81-2.73 (m, 1H), 2.63-2.59 (m, 2H), 2.39-2.28 (m, 2H), 2.09-2.07 (m, 2H), 1.87-1.77 (m, 2H), 1.37-1.32 (m, 6H), 1.29-1.26 (m, 3H). LCMS $[M+1]^+$: 608.3.

Comparative Embodiment 1

Preparation of 2-(4-(2-ethyl-3-((4-(4-fluorophenyl)thiazol-2-yl)(methyl)amino)-8-methylimidazo[1,2a]pyridin-6-yl)piperazin-1-yl)-1-(3-hydroxyazetidin-1-yl)aceton

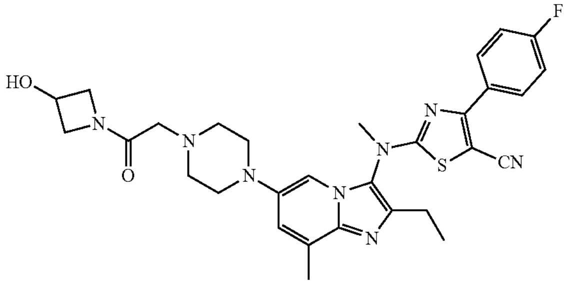

GLPG-1690

Comparative Embodiment 1 was synthesized according to Compound 7 in table III of PCT application WO 2014139882 A1.

Biological Test

Analysis In Vitro: LPC was Used as Substrate for Screening Enzyme Activity

Principle: Lysophosphatidylcholine (LPC) as substrate is hydrolyzed by using the activity of lysoPLD enzyme, to produce lysophosphatidic acid (LPA) and choline, which is oxidized to produce $H_2O_2$ under the action of choline oxidase. In presence of horse radish peroxidase (HPR), Amplex Red reagent is reacted with $H_2O_2$ in a quantitative chemistry ratio of 1 to 1, to produce strong fluorescence products, which are detected by a fluorescent quantitative test.

Experimental procedures: the compounds to be tested and the Comparative Embodiment 1 were dissolved in DMSO, respectively, to prepare 10 mM of stock solution, which was diluted in a gradient concentration of 3 times with DMSO from 10 mM, to generate 10 concentration gradients. The reaction buffer solution was used for preparing a mixed solution 1 of 2 ng/μl ATX, 2 U/ml HRP and 0.2 U/ml choline oxidase in a final concentration. 20 μl of the above mixed solution 1 was added to each hole of an experiment board, with 10 nl/hole. The compounds diluted with DMSO were transferred into an experiment board with Echo550. The reaction buffer solution was used for preparing a mixed solution 2 of 60 mM LPC and 400 μM Amplex Red in a final concentration. 20 μl of the above mixed solution 2 was added to each hole of the experiment board. After addition, the experiment board was shook for 30 seconds on a shaker, and incubated for 30 minutes. Envision was used to read the fluorescence signals with an exciting light at 530 nm and emitted light at 590 nm. Inhibition ratio of the compounds to enzyme reaction was calculated according to the ratio of fluorescence, and $IC_{50}$ of the compounds was analyzed and calculated by software, seeing Table 1.

TABLE 1

INHIBITORY ACTIVITY ANALYSIS OF THE COMPOUNDS AGAINST ATX, WITH LPC AS SUBSTRATE

| Compounds to be tested | LPC - $IC_{50}$ | Compounds to be tested | LPC - $IC_{50}$ |
|---|---|---|---|
| Embodiment 1 | ++++ | Embodiment 2 | ++++ |
| Embodiment 3 | +++ | Embodiment 4 | ++++ |
| Embodiment 5 | ++++ | Embodiment 6 | ++++ |
| Embodiment 7 | ++++ | Embodiment 8 | ++++ |
| Embodiment 9 | ++++ | Embodiment 10 | ++++ |
| Embodiment 11 | ++++ | Embodiment 12 | ++++ |
| Embodiment 13 | +++ | Embodiment 14 | ++++ |
| Embodiment 15 | +++ | Embodiment 16 | ++++ |
| Embodiment 17 | +++ | Embodiment 18 | +++ |
| Embodiment19 | ++++ | Embodiment 20 | ++++ |
| Embodiment 21 | ++++ | Embodiment 22 | ++++ |
| Embodiment 23 | ++++ | Embodiment 24 | +++ |
| Embodiment 25 | ++++ | Embodiment 26 | ++++ |
| Embodiment 27 | ++++ | Comparative Embodiment 1 | +++ |

+: >1000 nM;
++: 500-1000 nM;
+++: 100-500 nM;
++++: 0.01-100 nM

According to Table 1, the compounds of the present disclosure have a good inhibitory activity against ATX, and $IC_{50}$ values for most of the compounds are below 100 nM and are superior to that of Comparative Embodiment 1.

Pharmacokinetics Test in Mice

Male SD mice were selected for pharmacokinetics test study, plasma concentration at different time points were quantitatively determined by LC/MS/MS method after the mice were intravenously injected and orally administrated with the compounds to be tested, thereby evaluating pharmacokinetics characteristic of the compounds to be tested in SD mice.

SD mice (free food and drink, 6 to 8 weeks old) were intravenously administrated via a foot injection with a clear solution of the compounds to be tested, alternatively, SD mice (free food and drink, 6 to 8 week old) were intragastrically administrated with a suspension of the compounds to be tested. Blood samples were collected from the tail veins of the mice 0.083, 0.25, 0.5, 1, 2, 4, 6, 8, 10, and 24 hours after administration, and each sampling was 0.15 mL. All collected blood samples were placed into centrifuge tubes with EDTA-K2, turned upside and down to mix the anticoagulant with the blood well. The plasma was separated by centrifugation at 1500 g for 10 min at 4° C. within 30 mm. The plasma sample was transferred into a new centrifuge tube and stored at −90° C. to −60° C. until the analysis was performed. LC-MS/MS was used to measure the blood concentration of the compounds to be tested of the present disclosure, and the pharmacokinetic parameters, as well as absolute bioavailability, were calculated by a non-compartment model in Pharsight Phoenix 8.0 software, as shown in Table 2.

TABLE 2

Results of pharmacokinetics test of the compounds of the present disclosure

| | Intravenous injection (1 mg/kg) | | Oral administration (5 mg/kg) | | |
|---|---|---|---|---|---|
| Compounds to be tested | AUC (h*ng/mL) | $T_{1/2}$ (h) | AUC (h*ng/mL) | $T_{1/2}$ (h) | F |
| Embodiment 1 | 1670 | 4.18 | 5800 | 3.21 | 70% |
| Embodiment 2 | 972 | 2.84 | 2720 | 3.63 | 54% |
| Embodiment 7 | 1480 | 3.97 | 4810 | 2.81 | 65% |
| Embodiment 11 | 907 | 4.69 | 1730 | 4.396 | 42% |
| Embodiment 21 | 1040 | 3.32 | 5500 | 2.61 | 114% |
| Embodiment 22 | 649 | 4.56 | 1260 | 4.19 | 39% |
| Embodiment 23 | 1180 | 4.18 | 4190 | 3.93 | 70% |
| Embodiment 24 | 1170 | 2.14 | 2520 | 2.23 | 43% |
| Embodiment 25 | 732 | 3.11 | 1900 | 3.83 | 55% |

According to Table 2, the compounds of the present disclosure have a higher exposure and bioavailability.

In conclusion, the compound of the present disclosure has a great inhibitory activity against ATX and excellent efficacy in vivo and perfect pharmacokinetic properties, and well clinical application prospect.

Although the present invention has been disclosed in the form of embodiments and variations thereon, it will be understood that numerous additional modifications and variations could be made thereto without departing from the scope of the invention.

For the sake of clarity, it is to be understood that the use of ‘a’ or ‘an’ throughout this application does not exclude a plurality, and ‘comprising’ does not exclude other steps or elements.

The invention claimed is:

1. A compound having a structure of formula (II), or a pharmaceutically acceptable salt thereof:

(II)

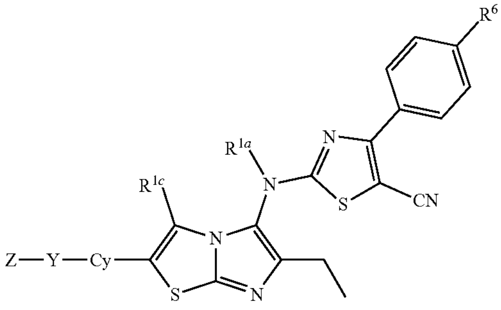

wherein,

Cy is

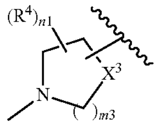

Y is —C(═O)—$(CH_2)_{t1}$—, or —N($R^{1b}$)C(═O)—$(CH_2)_{t1}$;

Z is is —$CH_2CH_2OH$, —$CH_2C(CH_3)_2OH$, —$CH_2C(CH_3)_2CH_2OH$, —$CH_2CH_2CN$, —$CH_2CHF_2$, —$CH(CH_3)CH_2OH$, —$C(CH_3)_2CH_2OH$, —$CH_2C(CH_3)_3$,

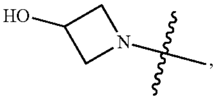

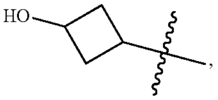

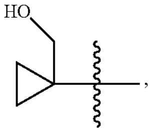

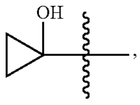

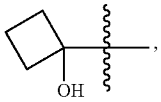

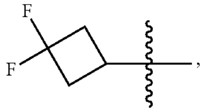

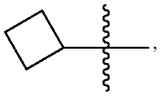

-continued

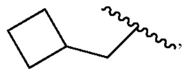

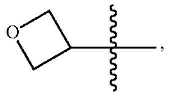

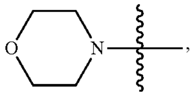

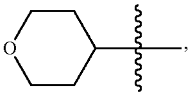

or

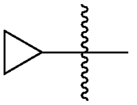

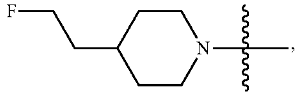

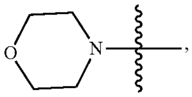

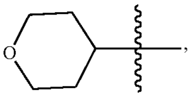

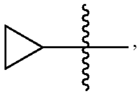

or

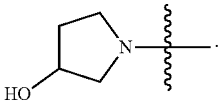

$R^{1a}$ is $C_{2-4}$ alkyl, $C_{1-4}$ haloalkyl, $C_{3-6}$ cycloalkyl, or $C_{3-6}$ cycloalkyl-C1-6 alkyl, wherein each of the $C_{2-4}$ alkyl, $C_{1-4}$ haloalkyl, $C_{3-6}$ cycloalkyl, or $C_{3-6}$ cycloalkyl-$C_{1-6}$ alkyl is optionally substituted with 1, 2, 3, 4, or 5 substituents independently selected from H, or D;

$R^{1b}$ is H or $C_{1-4}$ alkyl;

$R^{1c}$ is H;

$R^4$ is H;

$R^6$ is F; and t1 is 1.

2. The compound of claim 1, wherein $R^{1a}$ is H, ethyl, ethyl-D, isopropyl, trifluoromethyl, trifluoroethyl, hydroxyethyl, cyclopropyl, or cyclopropylmethyl.

3. The compound of claim 1, wherein $R^{1b}$ is H, methyl, or ethyl.

4. The compound of claim 1, wherein the compound has a structure selected from any one of the following:

(1)

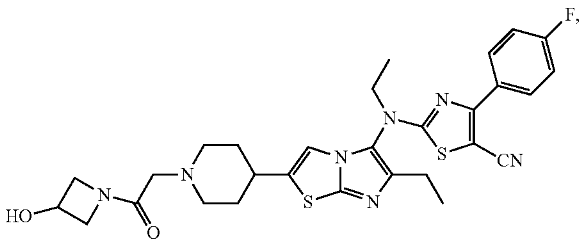

(2)

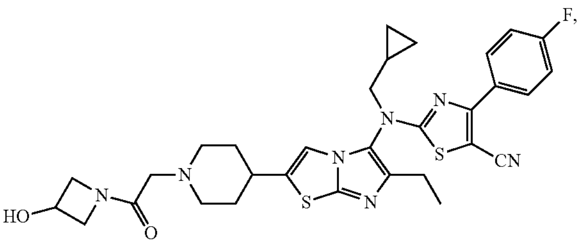

-continued
(4)
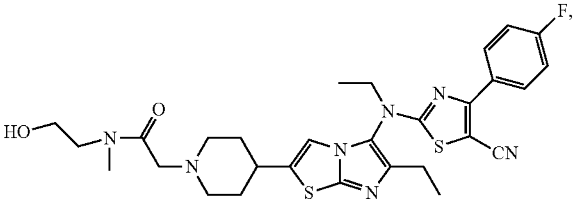
(5)
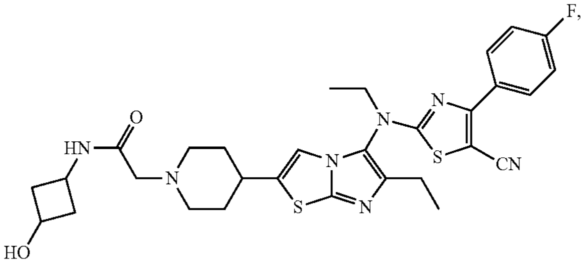
(6)
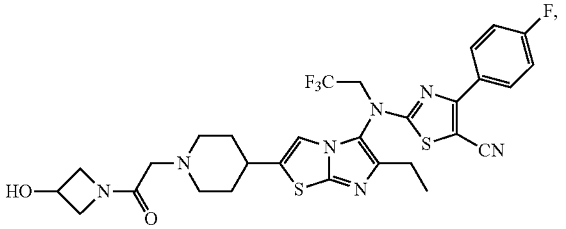
(7)
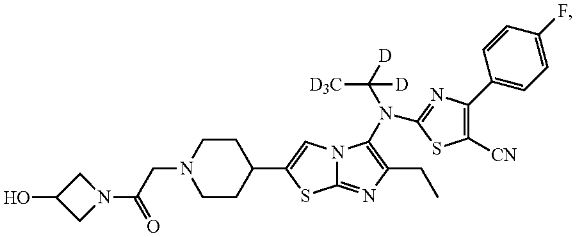
(8)
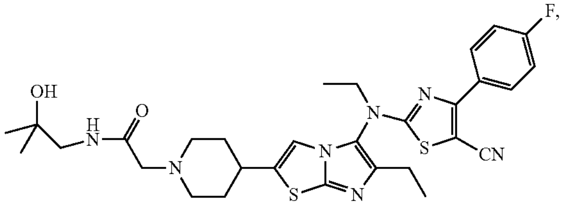
(9)
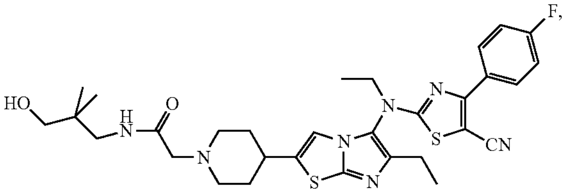
(10)
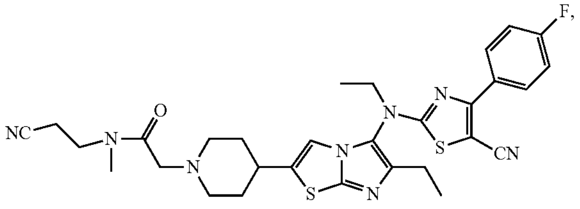
(11)
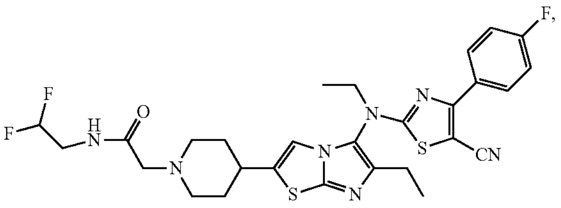
(12)
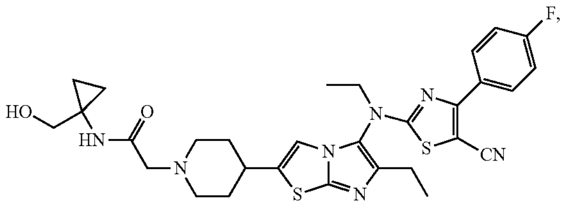
(14)
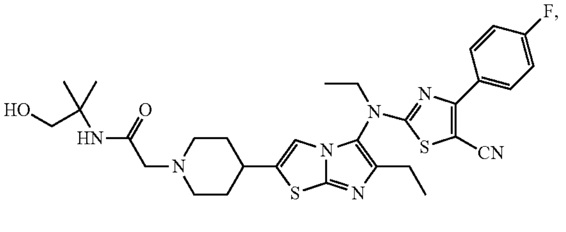

-continued (16)

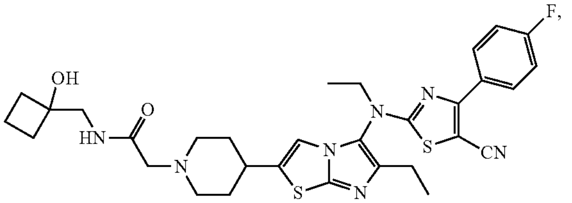

(19)

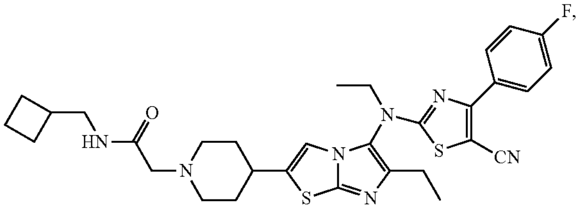

(20)

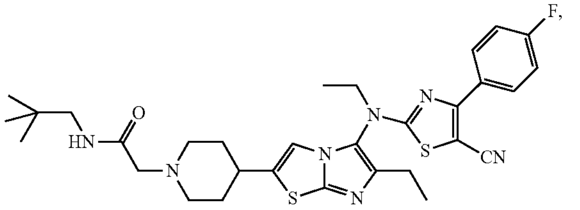

(21)

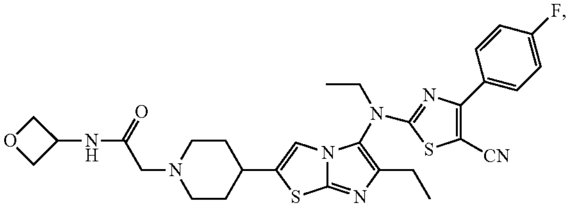

(22)

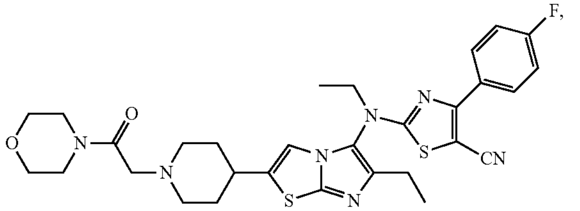

(30)

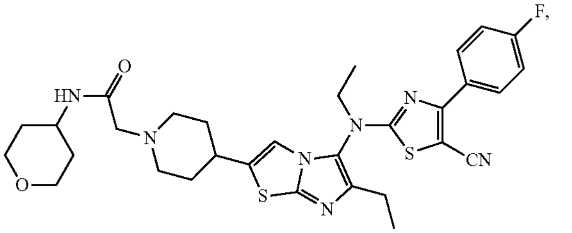

(31)

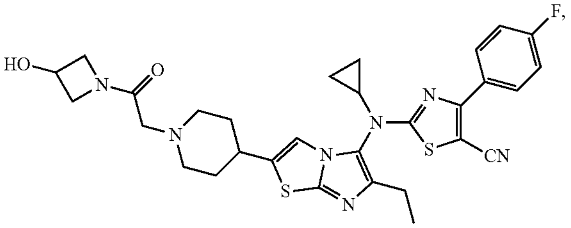

(32)

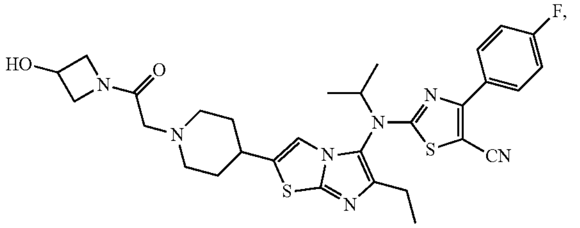

(33)

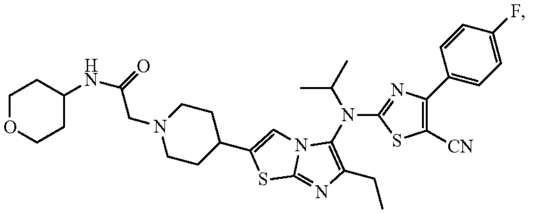

or (34)

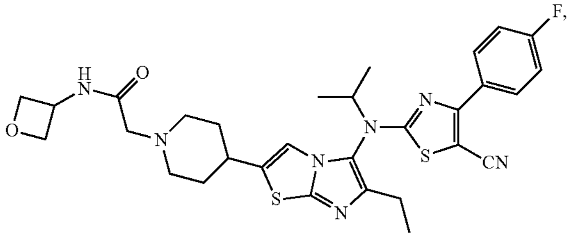

a pharmaceutically acceptable saltthereof.

5. A pharmaceutical composition, comprising the compound, or a pharmaceutically acceptable salt thereof of claim 1, and a pharmaceutically acceptable excipient, a diluent, or a carrier.

6. The pharmaceutical composition of claim 5, wherein the pharmaceutical composition further comprising an additional therapeutic agent.

7. A method of preventing or treating a disease with a pathological feature of Autotaxin overexpression in a mammal in need thereof, comprising administrating the compound of claim 1, or administrating a pharmaceutical composition comprising the compound, or a pharmaceutically acceptable, wherein the disease with a pathological feature of Autotaxin overexpression is pulmonary fibrosis, or hepatic fibrosis.

* * * * *